United States Patent
Curran et al.

(10) Patent No.: US 6,897,331 B2
(45) Date of Patent: May 24, 2005

(54) FLUOROUS TRIPHASE AND OTHER MULTIPHASE SYSTEMS

(75) Inventors: Dennis P. Curran, Pittsburgh, PA (US); Hiroyuki Nakamura, Shinjuku-Ku (JP); Ilhyong Ryu, Osaka (JP); Hiroshi Matsubara, Osaka (JP)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 10/094,345

(22) Filed: Mar. 8, 2002

(65) Prior Publication Data

US 2003/0125590 A1 Jul. 3, 2003

Related U.S. Application Data

(63) Continuation-in-part of application No. 09/877,944, filed on Jun. 8, 2001.

(51) Int. Cl.$^7$ ................................................. C07F 7/04
(52) U.S. Cl. ..................... 556/454; 556/450; 556/476; 556/485
(58) Field of Search ................................ 556/454, 450, 556/476, 485

(56) References Cited

U.S. PATENT DOCUMENTS

| | | | |
|---|---|---|---|
| 4,454,233 A | 6/1984 | Wang | |
| 5,401,847 A | 3/1995 | Glazer et al. | |
| 5,463,082 A | 10/1995 | Horvath et al. | |
| 5,777,121 A | 7/1998 | Curran et al. | |
| 5,798,032 A | 8/1998 | Khan et al. | |
| 5,859,247 A | 1/1999 | Curran et al. | |
| 6,156,896 A | 12/2000 | Curran et al. | |

FOREIGN PATENT DOCUMENTS

WO WO 02/100802 12/2002

OTHER PUBLICATIONS

Barthel–Rosa, L. P.; Gladysz, J. A. Chemistry in Fluorous Media: A User's Guide to Practical Considerations in the–Application of Fluorous Catalysts and Reagents. Coord. Chem. Rev.; 190–192;(1999), 587–605.

Cavazzini, M.; Montanari, F.; Pozzi, G.; Quici, S. Perfluorocarbon–Soluble Catalysts and Reagents and the Application of FBS (FluorousBiphase System) to Organic Synthesis J. Fluorine Chem.; 94 (1999); 183–193.

Chang, S. K; Hamilton, A. D., Molecular Recognition of Biologically Interesting Substrates: Synthesis of Artificial Receptors for Barbituates Employing Six Hydrogen Bonds J. Am. Chem. Soc., 1988, 110, 1318–1319.

Curran, D. P. Strategy–Level Separations in Organic Synthesis: From Planning to Practice. Angew. Chem., Int. Ed. Eng. 1998, 37, 1176–1196.

De Wolf, E.;Van Koten, G.; Deelman, B–J. Fluorous Phase Separation Techniques in Catalysis. Chem. Soc. Rev. 1999, 28, 37–41.

Fish, R. H. Fluorous Biphasic Catalysis: A New Paradigm for the Separation of Homogeneous Catalysts from their Reaction Substrates and Products. Chem. Eur.J. 1999, 5, 1677–1680.

Hope, E. G.; Stuart. A. M. Fluorous Biphase Cataysis. J. Fluorine Chem.; 100; (1999); 75–83.

Horvath, I. T. Fluorous Biphase Chemistry. Acc. Chem. Res. 1998, 31, 641–650.

Pereira, S. M. et al.; Perfluorohexane as a Nobel Reaction Medium for Bromination Reactions; Synth. Commun; 1995; 25; 1023–1026.

Zhu, D–W; A Novel Reaction Medium: Perfluorocarbon Fluids; Synthesis; 1993;953–954.

*Primary Examiner*—Samuel Barts
(74) *Attorney, Agent, or Firm*—Bartony & Hare, LLP

(57) ABSTRACT

A method of reacting a first non-fluorous compound to produce a second non-fluorous compound includes the steps of: contacting a first non-fluorous phase including the first non-fluorous compound with a first fluorous phase at a first phase interface, the first non-fluorous compound distributing between the first fluorous phase and the first non-fluorous phase; contacting the first fluorous phase with a second non-fluorous phase at a second phase interface; and including at least a third non-fluorous compound in the second non-fluorous phase that reacts with the first non-fluorous compound to produce the second non-fluorous compound, the second non-fluorous compound having a distribution coefficient less than the first non-fluorous compound. For example, the first non-fluorous compound can be dibromine or diiodine, and the second non-fluorous compound can be an alkene.

25 Claims, 14 Drawing Sheets

FLUOROUS TRIPHASE AND OTHER MULTIPHASE SYSTEMS

CROSS-REFERENCE TO RELATE APPLICATION

This application is a continuation in part of U.S. patent application Ser. No. 09/877,944, filed Jun. 8, 2001, the disclosure of which is incorporated herein by reference.

GOVERNMENT INTERESTS

This invention was made with government support under grant number GM031678 awarded by the National Institutes of Health. The government has certain rights in this invention.

BACKGROUND OF THE INVENTION

The present invention relates to fluorous triphase and other multiphase systems and, especially, to fluorous triphase and other multiphase systems for effecting reactions and/or separations.

References set forth herein may facilitate understanding of the present invention or the background of the present invention. Inclusion of a reference herein, however, is not intended to and does not constitute an admission that the reference is available as prior art with respect to the present invention.

In fluorous biphasic reaction methods, an organic substrate dissolved in an organic solvent and a fluorous catalyst (or precatalyst) dissolved in a fluorous solvent are contacted with any other needed reagents or reactants to form an organic product. Separation of the organic and fluorous liquid phases provides the product from the organic phase and the catalyst from the fluorous phase. See, for example, Horváth, I. T.; Rábai, *J. Science,* 266, 72 (1994); Horváth, I. T., *Acc. Chem. Res.,* 31, 641 (1998); and U.S. Pat. No. 5,463,082.

Since fluorous biphasic reactions were introduced to organic synthesis by Horváth and Rábai, much attention has been paid to the strategic new option of fluorous techniques for conducting organic reactions and for separating reaction mixtures. A review of fluorous techniques is provided in Curran, D. P., *Angew. Chem., Int. Ed. Engl.,* 37, 1175 (1998). In general, fluorous techniques in organic synthesis can be classified into three categories: (1) fluorous biphasic reactions as described above; (2) fluorous liquid-organic liquid separation; and (3) organic liquid-fluorous solid separation.

Although the usefulness of fluorous techniques has been extended substantially in recent years, it remains very desirable to develop improved fluorous reaction and separation methods and apparatuses.

SUMMARY OF THE INVENTION

In one aspect, the present invention provides a method of reacting a first compound to produce a second compound including the steps of: contacting a first non-fluorous phase including the first compound with a first fluorous phase at a first phase interface, the first compound distributing between the first fluorous phase and the first non-fluorous phase; contacting the first fluorous phase with a second non-fluorous phase at a second phase interface; and including at least a third compound in the second non-fluorous phase that reacts with the first compound to produce the second compound, the second compound having a distribution coefficient less than the first compound (and preferably distributing preferentially in the second non-fluorous phase). This method can, for example be used to separate the second compound from unreacted first compound wherein, for example, the first compound is of a fluorous nature and distributes more readily into (or transports, diffuses or migrates more quickly through) the fluorous phase than does the second compound. In general, the fluorous phase serves as a barrier to prevent the two non-fluorous phases from mixing, but molecules that can transport, diffuse or migrate through the fluorous phase can pass from one side to the other. As used herein, the term "transport" includes unaided movement, migration or diffusion of a chemical substance or diffusion or migration assisted by a reagent.

The fluorous liquid phase(s) of the present invention can, for example, include any number of fluorous liquids as known in the art, including fluorous solvents. As used herein, the term "fluorous liquid" refers generally to a liquid and/or a liquid mixture that is rich in carbon-fluorine bonds. As used herein, the term "fluorous solvent" refers generally to a solvent and/or a solvent mixture that is rich in carbon-fluorine bonds. Fluorous solvents include fluorocarbons (for example, perfluorohexane and perfluoroheptane), fluorohydrocarbons, fluorinated ethers (for example, perfluorobutyltetrahydrofuran) and fluorinated amines (for example, perfluorotriethyl amine), among others. In general, fluorous liquids and solvents have Hildebrand solubility parameters less than about 14 $MPa^{1/2}$. Many fluorous liquids and solvents are commercially available, and a partial list of commercially available and otherwise known fluorous liquids and solvents is contained in Barthel-Rosa, L. P.; Gladysz, J. A. "Chemistry in fluorous media: a user's guide to practical considerations in the application of fluorous catalysts and reagents" *Coord. Chem. Rev.,* 192, 587–605 (1999).

As used herein, the term "liquid" refers generally to phases that take the shape of their container without necessarily filling it (J. N. Murrell and E. A. Boucher, "Properties of Liquids and Solutions" Wiley, N.Y., 1982, pp1–3). Non-viscous liquids fill a container quickly, while liquid phases with a high viscosity may take a perceptible time to fill a container. Examples of high-viscosity fluorous liquids include, for example, oligomeric mixtures such as the Krytox series available from DuPont.

The term "liquid" also includes supported liquids wherein, for example, the liquid is included in the pore space of a macro-porous or micro-porous support (for example, a liquid membrane). The term "liquid" further includes gel phases, which are formed, for example, by adding a gelling agent to a liquid phase, and plasticized liquid phases. The term liquid also includes solutions of nominally pure liquids and other chemical species dissolved in or suspended in them. For example, such dissolved species can be other liquids, solids that form a pseudophase (for example, perfluoroalkane sulfonate of perfluoroalkane carboxylate surfactants which may form reverse micelles or other pseudophases), transport agents or carriers (for example, metal chelators, metal complexes, organic molecular receptors or nanoparticles).

Non-fluorous phases of the present invention can generally be any non-fluorous liquid or solvent as known in the art. As used herein, the terms "non-fluorous liquid" and "non-fluorous solvent" refers generally to organic and aqueous liquids and solvents, respectively, and/or to mixtures thereof. Preferred non-fluorous liquids have a Hildebrand solubility parameter greater than about 17 $MPa^{1/2}$, and more preferred non-fluorous liquids have a Hildebrand parameter greater than about 18 $MPa^{1/2}$. Water and other aqueous liquid mixtures are suitable non-fluorous liquids for use in the present invention, as are many organic liquids including, but not limited to, acetonitrile, ethyl acetate, ethanol, methanol, tetrahydrofuran, dimethyl formamide, dimethyl sulfoxide, toluene and benzene. Non-traditional organic liquids such as ionic liquids can also be used.

In the methods of the present invention, the fluorous mutliphasic system preferably does not become substantially homogeneous at any point in the process. In this regard, the fluorous and non-fluorous phases preferably remain substantially immiscible during the course of the process. However, some mixing or miscibility at the phase boundary (interface) between the fluorous and non-fluorous phases is allowable and may even be helpful to promote the contact of the fluorous and non-fluorous phases and thereby facilitate exchange of certain components between the respective phases. In addition, the non-fluorous phase may distribute into the fluorous phase altering its composition during a reaction, separation or reaction/separation procedure. Likewise, the fluorous phase may distribute into the non-fluorous phase, altering its composition. The conditions for miscibility or immiscibility of many fluorous and non-fluorous liquids and liquid mixtures are well known, and unknown pairings can often be predicted by differences in Hildebrand solubility parameters or can be readily determined experimentally.

In one embodiment, the first non-fluorous phase includes at least one compound other than the first compound. The other compound has a distribution coefficient less than the first compound and preferably distributes preferentially into the first non-fluorous phase. In this embodiment, the other compound(s) can be thought of as impurities. The higher distribution coefficient of the first compound (for example, as a result of increased or greater fluorous nature of the first compound) as compared to the other compound(s) results in a separation of the first compound from such "impurities" before and/or during the reaction step without a separate separation step/apparatus.

Preferably, the first compound has a distribution coefficient between approximately 0.01 and approximately 10 (as determined between the first fluorous phase and the first non-fluorous phase). More preferably, the first compound has a distribution coefficient between approximately 0.1 and approximately 5.0. Most preferably, the first compound has a distribution coefficient between approximately 0.5 and approximately 2.0.

As used herein, the distribution coefficient ($K_D$) is defined generally as the total concentration of a substance (for example, a molecule, molecular fragment, compound, ion, or complex) in the fluorous phase divided by the total concentration of the substance in the non-fluorous phase, at equilibrium. An experimental measurement of the concentration of a substance at equilibrium with two immiscible liquid phases yields the distribution coefficient, as shown by the experiments in Examples 1 and 2 of the Experimental Examples set forth below. If that substance does not participate in chemical or physical equilibria other than partitioning, the distribution coefficient is the same as the partition coefficient. The partition coefficient reflects the relative tendency of the substance to dissolve in each of the two immiscible phases at equilibrium. If that substance enters into other chemical or physical equilibria, for example protonation/deprotonation, metal binding/chelation, association with a receptor, micellization, etc., then the distribution coefficient represents the net effect of all of the equilibria; namely the partitioning equilibria and all other chemical and physical equilibria in which the substance takes part. In cases where an equilibrium is not reached, for example, as a result of an ongoing chemical reaction that continually displaces the equilibrium, the measurement of a distribution coefficient may not be practical, and experiments to measure the relative concentrations of a substance instead provide an operational non-equilibrium distribution ratio.

In general, a substance that distributes preferentially into the fluorous phase has a distribution coefficient greater than 1 (and often much greater than 1), and a substance that distributes preferentially into a non-fluorous phase (for example, an organic phase) has a distribution coefficient less than 1 (and often much less than 1).

To effect separation, the distribution coefficient(s) of one or more compounds other than the first compound (as measured between the first fluorous phase the first non-fluorous phase) in the methods of the present invention are less than the distribution coefficient of the first compound, resulting in faster transport of the first compound through the first fluorous phase. The distribution coefficient(s) of other compound(s) are preferably no greater than two times less than (or no greater than ½ of) the distribution coefficient of the first compound. More preferably, the distribution coefficient(s) of other compound(s) are no greater than five times less than (or no greater than ⅕ of) the distribution coefficient of the first compound. Most preferably, the distribution coefficient(s) of other compound(s) are no greater than ten times less than (or no greater than 1/10 of) the distribution coefficient of the first compound.

Likewise, the distribution coefficient(s) of the second compound and other product compounds (as measured between the first fluorous phase and the second non-fluorous phase) in the methods of the present invention are less than the distribution coefficient of the first compound (as measured between the first fluorous phase the first non-fluorous phase) to minimize back transport of the second compound through the first fluorous phase. The distribution coefficients of the second compound and any other product compound are preferably no greater than two times less than (or no greater than ½ of) the distribution coefficient of the first compound. More preferably, the distribution coefficient of the second compound is no greater than five times less than (or no greater than ⅕ of) the distribution coefficient of the first compound. Most preferably, the distribution coefficient of the second compound is no greater than ten times less than (or no greater than 1/10 of) the distribution coefficient of the first compound.

The first compound can, for example, include a fluorous group. Such a first compound can, for example, react with the third compound to produce the second compound, which is less fluorous in nature than the first compound. The reaction of the first compound and the third compound can also produce a fluorous compound (for example, a fluorous byproduct) which preferably distributes preferentially from the second non-fluorous phase into the fluorous phase, thereby being separated from the second compound which preferably distributes preferentially into the second non-fluorous phase. In general, the fluorous compound preferably has a distribution coefficient substantially greater than 1 (as measured between the first fluorous phase and the second non-fluorous phase). More preferably, the fluorous compound or byproduct has a distribution coefficient greater than 3. Most preferably, the fluorous compound or byproduct has a distribution coefficient greater than 10. If the fluorous byproduct is not separated from the second compound to a sufficient extent, other fluorous separation techniques (for example, liquid-liquid separation(s) and/or solid-liquid separation(s)) can be used to effect separation. The method can also include the step of tagging the fluorous group onto a precursor compound to synthesize a fluorous-tagged first compound.

As used herein, the terms "fluorous tagging" or "fluorous-tagged" refers generally to attaching a fluorous moiety or group (referred to as a "fluorous tagging moiety," "fluorous tagging group" or simply "fluorous tag") to a compound to create a "fluorous-tagged compound". Preferably, the fluorous tagging moiety is attached via covalent bond. However, other effective attachments such as ionic bonding, chelation or complexation can also be used. Fluorous tagging moieties facilitate separation of fluorous tagged compounds from other compounds as a result of differences in the fluorous nature of the compounds.

As used herein, the term "fluorous", when used in connection with an organic (carbon-containing) molecule, moiety or group, refers generally to an organic molecule, moiety or group having a domain or a portion thereof rich in carbon-fluorine bonds (for example, fluorocarbons, fluorohydrocarbons, fluorinated ethers and fluorinated amines). The terms "fluorous-tagged reagent" or "fluorous reagent," thus refer generally to a reagent comprising a portion rich in carbon-fluorine bonds. As used herein, the term "perfluorocarbons" refers generally to organic compounds in which all hydrogen atoms bonded to carbon atoms have been replaced by fluorine atoms. The terms "fluorohydrocarbons" and "hydrofluorocarbons" include organic compounds in which at least one hydrogen atom bonded to a carbon atom has been replaced by a fluorine atom. Fluorous moieties and the attachment of fluorous moieties to organic compounds are discussed, for example, in U.S. Pat. Nos. 5,859,247 and 5,777,121, and in U.S. patent application Ser. Nos. 09/506,779, 09/565,087, 09/602,105, 09/952, 188 and 09/877,944, the disclosures of which are incorporated herein by reference.

Non-fluorous compounds, reactants or reagents do not have a domain or a portion thereof rich in carbon-fluorine bonds. Preferably, non-fluorous compounds reactants or reagents have five fluorines or fewer, more preferably non-fluorous compounds have three fluorines or fewer, and most preferably, non-fluorous compounds have one or no fluorines.

In another embodiment, the method further includes the step of contacting the second non-fluorous phase with a second fluorous phase at a third phase interface. In this embodiment, the method can also include the step of contacting the second fluorous phase with a third non-fluorous phase at a fourth phase interface. The method can thus include a series of reaction and/or separations as described above and below.

In another aspect, the present invention also provides a method of reacting a first compound with at least a second compound to produce a third compound including the steps of: contacting a first non-fluorous phase including the first compound and the second compound with a first fluorous phase at a first phase interface; contacting the first fluorous phase with a second non-fluorous phase at a second phase interface; and including at least one reagent (for example, a catalyst) to promote the reaction between the first compound and the second compound in the second non-fluorous phase, the reagent or catalyst distributing between the first fluorous phase and the second non-fluorous phase. In general, at least one of the first compound, the second compound and the third compound, has a distribution coefficient less than the reagent or catalyst. Preferably, all of the first compound, the second compound and the third compound, have a distribution coefficient less than the reagent or catalyst.

In another aspect, the present invention provides method of reacting a first compound to produce a second compound including the steps of: contacting a first non-fluorous phase including a first compound with a first fluorous phase at a first phase interface, the fluorous phase including at least one fluorous phase reagent that interacts with the first compound to form one or more fluorous intermediates; contacting the first fluorous phase with a second non-fluorous phase at a second phase interface; and including at least a third compound in the second non-fluorous phase that reacts with the fluorous intermediate or with the first compound to produce a product compound that preferably distributes preferentially in the second non-fluorous phase. The fluorous phase reagent preferably has a distribution coefficient (as, for example, measured between the fluorous phase and the first non-fluorous phase) of greater than approximately 1. More preferably, fluorous phase reagent preferably has a distribution coefficient greater than approximately 3. Most preferably, fluorous phase reagent preferably has a distribution coefficient greater than approximately 10. In general, the fluorous intermediate has a greater distribution coefficient than does the first compound.

The fluorous intermediate(s) can, for example, interact with the third compound in the fluorous phase (generally, in the vicinity of the second phase interface), at the second phase interface and/or in the second non-fluorous phase. The first compound can also be released by the fluorous intermediate(s) in the fluorous phase (generally, in the vicinity of the second phase interface), at the second phase interface and/or in the second non-fluorous phase wherein the first compound reacts with the third compound.

As used herein, the term "interact" refers, for example, to a chemical reaction to form or break a chemical bond between the first compound and the fluorous reagent, to formation or breakage of another type of bond or attractive interconnection between the first compound and the fluorous phase reagent, or to micellar interrelation between the first compound and the fluorous reagent. For example, a covalent or ionic bond can be formed between the reagent and the first compound. Other types of bonds or attractive interactions include non-covalent bonds such as hydrogen bonding, dipole-dipole interactions and van der Waals forces. In general, any type of interaction, bond or attractive force that is suitably strong or durable to permit the fluorous intermediate to function as a unit for transport or to facilitate transport through the fluorous phase can be used. In general, the interaction between the first compound and the fluorous phase reagent acts to draw the first compound into the fluorous phase from the first non-fluorous phase and facilitates transport of the fluorous intermediate (for example, a first compound/fluorous reagent aggregate) toward the second organic phase.

The term "fluorous phase reagent," as used herein refers generally to a chemical entity or physiochemical structure (for example, a micellar structure or particulate structure) that is suitable to interact with the first compound to form an intermediate entity or structure having a higher distribution coefficient than the first compound as described above. In one embodiment, the fluorous phase reagent can be a catalyst. For example, a fluorous catalyst that catalyzes a reaction between the second compound and the third compound can first form a fluorous complex with the first compound. The fluorous complex facilitates transport of the first compound through the fluorous phase toward the second organic phase. In other embodiments, the fluorous phase reagent can, for example, be a fluorous receptor, host or transport agent.

The first non-fluorous phase can include at least one compound other than the first compound. The other compound(s) preferably distribute preferentially into the first non-fluorous phase. The other compound(s) are preferably substantially non-reactive and non-interactive with the fluorous reagent. The interaction of the first compound with the reagent thus preferentially transports the first compound or other compounds derived from reaction thereof to the second non-fluorous phase via the first fluorous phase.

To carry out a series of reactions and/or separations as described here, the method can further include the step of contacting the second non-fluorous phase with a second fluorous phase at a third phase interface. The second fluorous phase can be contacted with a third non-fluorous phase at a fourth phase interface and so on.

Fluorous phase reagents can also be used to effect a separation with or without a reaction in the second non-fluorous phase. In that regard, the present invention provides in another aspect a method of separating a mixture of at least a first compound and a second compound comprising the steps of: contacting a first non-fluorous phase including the first compound and the second compound with a first fluorous phase at a first phase interface, the fluorous phase including a fluorous reagent that selectively interacts with the first compound to form a fluorous intermediate; and contacting the first fluorous phase with a second non-fluorous phase at a second phase interface.

The distribution coefficients of the second or other compounds in the first non-fluorous phase (as measured between the first fluorous phase and the first non-fluorous phase) are preferably no greater than two times less than (or no greater than ½ of) the distribution coefficient of the fluorous intermediate. More preferably, the distribution coefficients of the second or other compounds are no greater than five times less than (or no greater than ⅕ of) the distribution coefficient of the fluorous intermediate. Most preferably, the distribution coefficients of the second or other compounds are no greater than ten times less than (or no greater than ¹/₁₀ of) the distribution coefficient of the fluorous intermediate.

In another aspect, the present invention provides a method of separating a mixture of at least a first compound and a second compound including the steps of: contacting a mixture of the of the first compound and the second compound in a first non-fluorous phase with a first fluorous phase at a first phase interface, the first compound distributing between the first fluorous phase and the first non-fluorous phase, the second compound having a distribution coefficient less than the first compound (and preferably distributing preferentially in the first non-fluorous phase); and contacting the fluorous phase with a second non-fluorous phase at a second phase interface.

The method can further include the step of selectively reacting a precursor compound with a fluorous tagging compound to produce the first compound, which is a fluorous-tagged compound.

The distribution coefficients of the second or other compounds in the first non-fluorous phase (as measured between the first fluorous phase and the first non-fluorous phase) are preferably no greater than two times less than (or no greater than ½ of) the distribution coefficient of the first compound. More preferably, the distribution coefficients of the second or other compounds are no greater than five times less than (or no greater than ⅕ of) the distribution coefficient of the first compound. Most preferably, the distribution coefficients of the second or other compounds are no greater than ten times less than (or no greater than ¹/₁₀ of) the distribution coefficient of the first compound.

The method can also include the step of including at least third compound in the second non-fluorous phase that reacts with a fluorous-tagged first compound to produce a fourth compound of reduced fluorous nature compared to the first, fluorous-tagged, compound, the fourth compound preferably distributing preferentially in the second non-fluorous phase. The fourth compound can be chemically the same as the precursor compound (that is, regeneration of the precursor compound) or chemically different from the precursor compound.

The method can also include the step of contacting the second non-fluorous phase with a second fluorous phase at a third phase interface. Once again, the second fluorous phase can be contacted with a third non-fluorous phase at a fourth phase interface and so on.

The methods of the present invention can, for example, be applied to separate a mixtures of enantiomers. Many stereoselective reactions, reagents and catalysts are known to those skilled in the art. For example, see Eliel, E. L.; Wilen, S. *Stereochemistry of Organic Compounds;* Wiley-Interscience: New York, 1994. Known and new reactions and reagents can be rendered fluorous or fluorous tagged as described herein and in U.S. Pat. Nos. 5,859,247, 5,777,121, U.S. patent application Ser. No. 09/506,779, and U.S. Provisional Patent Application Serial No. 60/281,646. In the methods of the present invention, at least one enantiomer of, for example, a racemic mixture of enantiomers can be preferentially converted to a fluorous or fluorous-tagged product. The reaction and/or separation methods of the present invention can then be used to separate the mixture.

In another aspect, the present invention provides an apparatus (for example, for separation and/or reaction of compounds) including a first non-fluorous phase in contact with a first fluorous phase at a first phase interface and a second non-fluorous phase in contact with the first fluorous phase at a second phase interface. Preferably, the first fluorous phase is a liquid phase.

The first non-fluorous phase can, for example, be in an upper portion of a first leg of a U-tube, the second non-fluorous phase can be in the upper portion of a second leg of the U-tube, and the first fluorous phase can be positioned within the U-tube between the first non-fluorous phase and the second non-fluorous phase. In one embodiment, the first non-fluorous phase includes a first stirring member therein, the first fluorous phase includes a second stirring member therein and the second non-fluorous phase includes a third stirring member therein. The stirring member can be used to perturb the phase interfaces to enhance exchange of certain components between the phases.

To carry out a series of reactions and/or separations as described herein, the second non-fluorous phase can be placed in contact with a second fluorous phase at a third phase interface, and the second fluorous phase can be placed in contact with a third non-fluorous phase at a fourth phase interface and so on.

Although the reaction and/or separation methods and the devices of the present invention are well suited for use in systems including at least one fluorous component, the methods and devices of the present invention can also be used in systems including no fluorous component except for the fluorous phase itself. In that regard, the present invention provides a method of reacting a first non-fluorous compound to produce a second non-fluorous compound including the steps of: contacting a first non-fluorous phase including the first non-fluorous compound with a first fluorous phase at a first phase interface, the first non-fluorous compound dis tributing between the first fluorous phase and the first non-fluorous phase; contacting the first fluorous phase with a second non-fluorous phase at a second phase interface; and including at least a third non-fluorous compound in the second non-fluorous phase that reacts with the first non-fluorous compound to produce the second non-fluorous compound, the second non-fluorous compound having a distribution coefficient less than the first non-fluorous compound. Preferably, the second non-fluorous compound resides or distributes preferentially in the second non-fluorous phase. For example, the first non-fluorous compound can be dibromine ($Br_2$), and the second non-fluorous compound can be an alkene or an alkyne.

The second non-fluorous phase of the above processes may also include other non-fluorous components, for example, reagents or catalysts to promote or participate in the reaction between the first non-fluorous compound and the third non-fluorous compound. In these processes, the second non-fluorous compound and any other non-fluorous components preferably reside predominately in the second non-fluorous phase as a result of their low distribution coefficient into the fluorous phase. This distribution coefficient is preferably greater than 10 more preferably greater than 50, and even more preferably greater than 100. Many typical organic and inorganic compounds meet these needs.

The present invention also provides a method of reacting a first non-fluorous compound with at least a second non-fluorous compound to produce a third non-fluorous compound including the steps of: contacting a first non-fluorous phase including the first non-fluorous compound and the second non-fluorous compound with a first fluorous phase at a first phase interface; contacting the first fluorous phase with a second non-fluorous phase at a second phase interface; and including at least one non-fluorous reagent or catalyst to promote the reaction between the first non-fluorous compound and the second non-fluorous compound in the second non-fluorous phase, the non-fluorous reagent or catalyst distributing between the first fluorous phase and the second non-fluorous phase. In general, at least one of the first non-fluorous compound, the second non-fluorous compound and the third non-fluorous compound has a distribution coefficient less than the non-fluorous reagent or catalyst. Preferably, the first non-fluorous compound, the second non-fluorous compound and the third non-fluorous compounds have distribution coefficients less than the non-fluorous reagent or catalyst to, for example, the extent described above.

The non-fluorous catalyst can, for example, be a metal halide. Such catalysts are useful, for example, to catalyze a Friedel-Crafts reaction (for example, an acylation) between the first non-fluorous compound and the second non-fluorous compound). An example of a suitable metal halide catalyst is tin tetrachloride.

Still further, the present invention provides a method of separating a mixture of at least a first non-fluorous compound and a second non-fluorous compound including the steps of: contacting a mixture of the of the first non-fluorous compound and the second non-fluorous compound in a first non-fluorous phase with a first fluorous phase at a first phase interface, the first non-fluorous compound distributing between the first fluorous phase and the first non-fluorous phase, the second non-fluorous compound having a distribution coefficient less than the first non-fluorous compound; and contacting the fluorous phase with a second non-fluorous phase at a second phase interface.

In general, in the fluorous multiphasic systems of the present invention, one or more fluorous phases separate other non-fluorous phases. As a result of differing distribution coefficients between system components, controlled distribution or transportation of one or more system components (for example, compounds, reactants, reagents, catalysts, etc.) through the fluorous phase enables, for example, separation or concurrent reaction and separation of system components. Moreover, distribution or transportation of a system component through a fluorous phase can be used to control the rate of delivery of that component to a non-fluorous phase to, for example, control a rate of a reaction in that non-fluorous phase. The present invention, thus provides generally a method of controlling the distribution of one or more components from one non-fluorous phase to another non-fluorous phase through placement of an intermediate fluorous phase therebetween. The novel fluorous multiphasic systems, methods and apparatus of the present invention, thereby facilitate and/or enhance many exiting or new reactions and/or separations.

DETAILED DESCRIPTION OF THE INVENTION

In several representative examples of the present invention, a detagging/deprotection reaction of the fluorinated silylethers as set forth in equation (1) was studied using various three-phase or "triphasic" systems of the present invention.

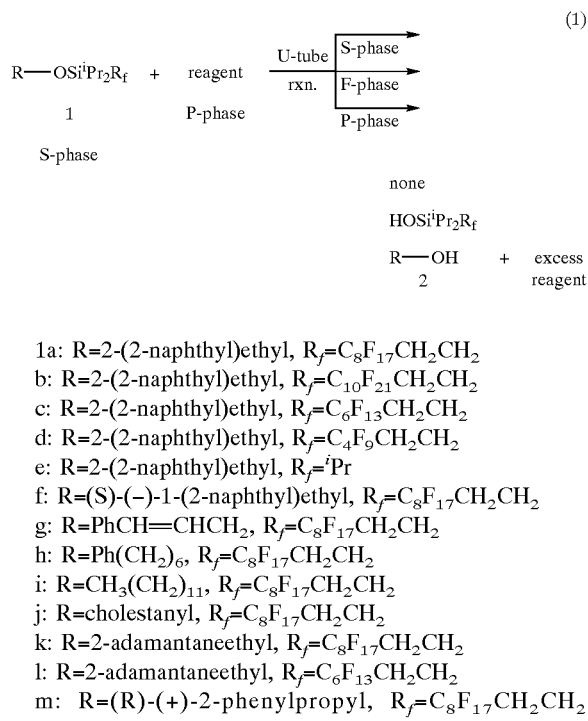

Figure 1:
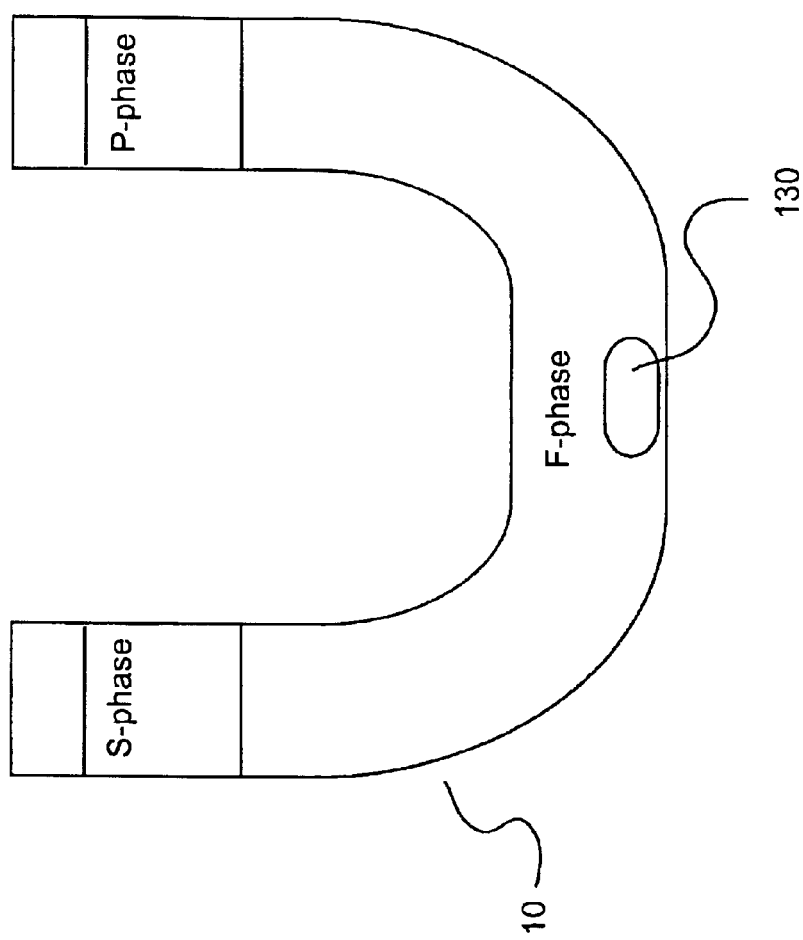
FIG. 1 illustrates an embodiment of a triphasic U-tube reaction/separation apparatus of the present invention including an upper first organic phase (S-phase) in a first leg of the U-tube, an upper second organic phase (P-phase) in a second leg of the U-tube and a fluorous phase (F-phase) positioned intermediate between the first organic phase and the second organic phase.

1a: R=2-(2-naphthyl)ethyl, $R_f$=$C_8F_{17}CH_2CH_2$
b: R=2-(2-naphthyl)ethyl, $R_f$=$C_{10}F_{21}CH_2CH_2$
c: R=2-(2-naphthyl)ethyl, $R_f$=$C_6F_{13}CH_2CH_2$
d: R=2-(2-naphthyl)ethyl, $R_f$=$C_4F_9CH_2CH_2$
e: R=2-(2-naphthyl)ethyl, $R_f$=$^iPr$
f: R=(S)-(−)-1-(2-naphthyl)ethyl, $R_f$=$C_8F_{17}CH_2CH_2$
g: R=PhCH=CHCH$_2$, $R_f$=$C_8F_{17}CH_2CH_2$
h: R=Ph(CH$_2$)$_6$, $R_f$=$C_8F_{17}CH_2CH_2$
i: R=CH$_3$(CH$_2$)$_{11}$, $R_f$=$C_8F_{17}CH_2CH_2$
j: R=cholestanyl, $R_f$=$C_8F_{17}CH_2CH_2$
k: R=2-adamantaneethyl, $R_f$=$C_8F_{17}CH_2CH_2$
l: R=2-adamantaneethyl, $R_f$=$C_6F_{13}CH_2CH_2$
m: R=(R)-(+)-2-phenylpropyl, $R_f$=$C_8F_{17}CH_2CH_2$ In these studies, the fluorinated silyl ether 1 was charged to one side of U-tube 10 of FIG. 1 in an organic solvent (substrate phase or S-phase; sometimes also referred to herein as the first non-fluorous phase) and the reagent for the cleavage was charged to another side of U-tube 10 in an organic solvent (product phase or P-phase; sometimes also referred to a the second non-fluorous phase). The two phases were separated by a fluorous liquid/solvent (fluorous phase or F-phase) as illustrated in FIG. 1. The fluorinated silyl ether migrated from S-phase to P-phase over time. When the fluorinated silyl ether reached the P-phase, it underwent a reaction (in this example, a detagging or deprotection reaction) by a cleavage reagent in the P-phase to yield an organic alcohol 2 and a fluorous silyl by-product (HOSi$^i$Pr$_2$Rf). The fluorous by-product distributed or partitioned back to the F-phase and the organic alcohol was "trapped" in the P-phase since the partition coefficient ($K_P$; equivalent to the distribution coefficient $K_D$ in this case) of the organic alcohol (ROH) is relatively low and the transport rate of the alcohol was small. The term partition coefficient as used herein is defined generally as $[M]_{Fluorous}/[M]_{Non\text{-}Fluorous}$ or $[M]_F/[M]_{Non\text{-}F}$. In essence, the chemical energy of the desilylation reaction drives the transport of a molecule from the left side to the right side in a non-equilibrium fashion. Since transport is separation, the triphasic system of the present invention effects a reaction preceded by or concomitant with a separation.

The results of several studies of the triphasic reaction of equation (1) are shown in Table I. The silyl ether 1a was chosen as a model substrate for several experiments (entries 1–9) and FC-72 was used in F-phase in all experiments of Table I. FC-72™, a common fluorocarbon fluid, is a mixture of $C_6F_{14}$ isomers with a boiling point of 56° C. FC-72 is commercially available from 3M Specialty Materials of St. Paul, Minn.

According to the partition coefficients ($K_P$s) of 1a toward various organic solvents and the transfer rates of the corresponding alcohol 2a in the triphasic media, acetonitrile (MeCN) was chosen as a solvent for the S-phase in the studies of Table I.

TABLE I

Deprotection of the Fluorinated Silylethers 1 Using Triphasic Reaction System

| entry | substrate | $K_P^a$ | reagent$^b$ | solvent (R-phase) | time | product, 2 | yield (%) | ratio of 2 (P-/S-phase) |
|---|---|---|---|---|---|---|---|---|
| 1 | 1a | 0.92 | HCl | MeOH—H$_2$O$^c$ | 4 d | 2a | 92 | 54/46 |
| 2 | 1a | | AcOH | MeOH—H$_2$O$^c$ | 6 d | 2a | 54$^d$ | 96/4 |
| 3 | 1a | | CsF | MeOH—H$_2$O$^c$ | 4 d | 2a | 80$^e$ | >99/1 |
| 4 | 1a | | H$_2$SO$_4$ | MeOH—H$_2$O$^c$ | 4 d | 2a | 92 | >99/1 |
| 5 | 1a | | H$_2$SiF$_6$ | MeOH | 2 d | 2a | 96 | >99/1 |
| 6 | 1a | | H$_2$SiF$_6$ | DMF | 1 d | 2a | 89 | >99/1 |
| 7 | 1a | | H$_2$SiF$_6$ | MeCN | 1 d | 2a | 99 | 91/9 |
| 8 | 1a | | H$_2$SO$_4$ | MeOH—H$_2$O$^c$ | 18 h | 2a | 97 | >99/1 |
| 9 | 1a | | H$_2$SiF$_6$ | MeOH | 20 h | 2a | 92 | >99/1 |
| 10 | 1b | 2.7 | H$_2$SiF$_6$ | MeOH | 6 d | 2a | >99 | 84/16 |
| 11 | 1c | 0.39 | H$_2$SiF$_6$ | MeOH | 1.5 d | 2a | 90 | 86/14 |
| 12 | 1d | 0.12 | H$_2$SiF$_6$ | MeOH | 3 d | 2a | 96 | 67/33 |
| 13 | 1e | 0.015 | H$_2$SiF$_6$ | MeOH | 7 d | 2a | 97 | 59/41 |
| 14 | 1f | 1.5 | H$_2$SiF$_6$ | MeOH | 2 d | 2f | 87 | 98/2 |
| 15 | 1g | 1.3 | H$_2$SiF$_6$ | MeOH | 1.5 d | 2g | 90 | >99/1 |
| 16 | 1h | 0.72 | H$_2$SiF$_6$ | MeOH | 3 d | 2h | 95 | 95/5 |
| 17 | 1i | 8.2 | H$_2$SiF$_6$ | MeOH | 7 d | 2i | 91 | 84/16 |

TABLE I-continued

Deprotection of the Fluorinated Silylethers 1 Using Triphasic Reaction System

| entry | substrate | $K_P{}^a$ | reagent[b] | solvent (R-phase) | time | product, 2 | yield (%) | ratio of 2 (P-/S-phase) |
|---|---|---|---|---|---|---|---|---|
| 18 | 1j | 5.0 | $H_2SiF_6$ | MeOH | 7 d | 2j | 38[f] | 74/26 |
| 19 | 1k | 5.7 | $H_2SiF_6$ | MeOH | 7 d | 2k | >99 | 91/9 |
| 20 | 1l | 1.9 | $H_2SiF_6$ | MeOH | 1.5 d | 2k | 93 | 96/4 |

[a] $K_P$ of substrates 1 was measured between FC-72 and MeOH.
[b] The amount of reagents used is as follows: HCl (2 equiv) in entry 1; AcOH (35 equiv) in entry 2; CsF (3 equiv) in entry 3; $H_2SO_4$ (1 equiv) in entries 4 and 8; $H_2SiF_6$ (2 equiv) in entries 5–7 and 9–20.
[c] The ratio of MeOH/$H_2O$ is 20/1.
[d] 1a was recovered in 36% and 8% yields from S- and F-phases, respectively.
[e] 1a was recovered in ~10% yield from F-phase.
[f] The reaction was not completed even after 7 days and 1j was recovered in 55% yield from F-phase.

In several experiments, the substrate 1a was dissolved in acetonitrile and placed in the S-phase. The reagent was dissolved in an organic solvent and placed in the P-phase. Using HCl as a cleavage reagent, 2a was obtained in 92% total yield after 4 days. However, the product was observed in almost equal amounts in both S-phase and the P-phase. Moreover, the S-phase was found to be acidic at the end of the reaction, indicating that HCl transferred from the P-phase to the S-phase through the FC-72 F-phase.

In general, the cleavage reagent HCl transports through the F-phase more quickly than preferred in the present invention. In other words, HCl has a higher $K_D$ (or $K_P$) than desirable for use as a P-phase (or second non-fluorous phase) reagent in the present invention. Preferably, the P-phase reagent transports very slowly through the F-phase or has low $K_D$ (or $K_P$). Thus, the substrate is preferably transported through the F-phase to the P-phase substantially more quickly than the P-phase reagent is transported through the F-phase from the P-phase to the S-phase.

Various reagents were thus examined to study the triphasic deprotection reactions (see entries 1–5 in Table 1). In the studies of Table I, using $H_2SO_4$ or $H_2SiF_6$ and aqueous MeOH as the P-Phase organic solvent, 2a was observed substantially only in P-phase with high yields (see, for example, entries 4 and 5). Various solvents were also examined using $H_2SiF_6$ as the reagent in P-phase. MeOH and DMF were found to be effective for the reaction (see entries 5–7).

Figure 2:
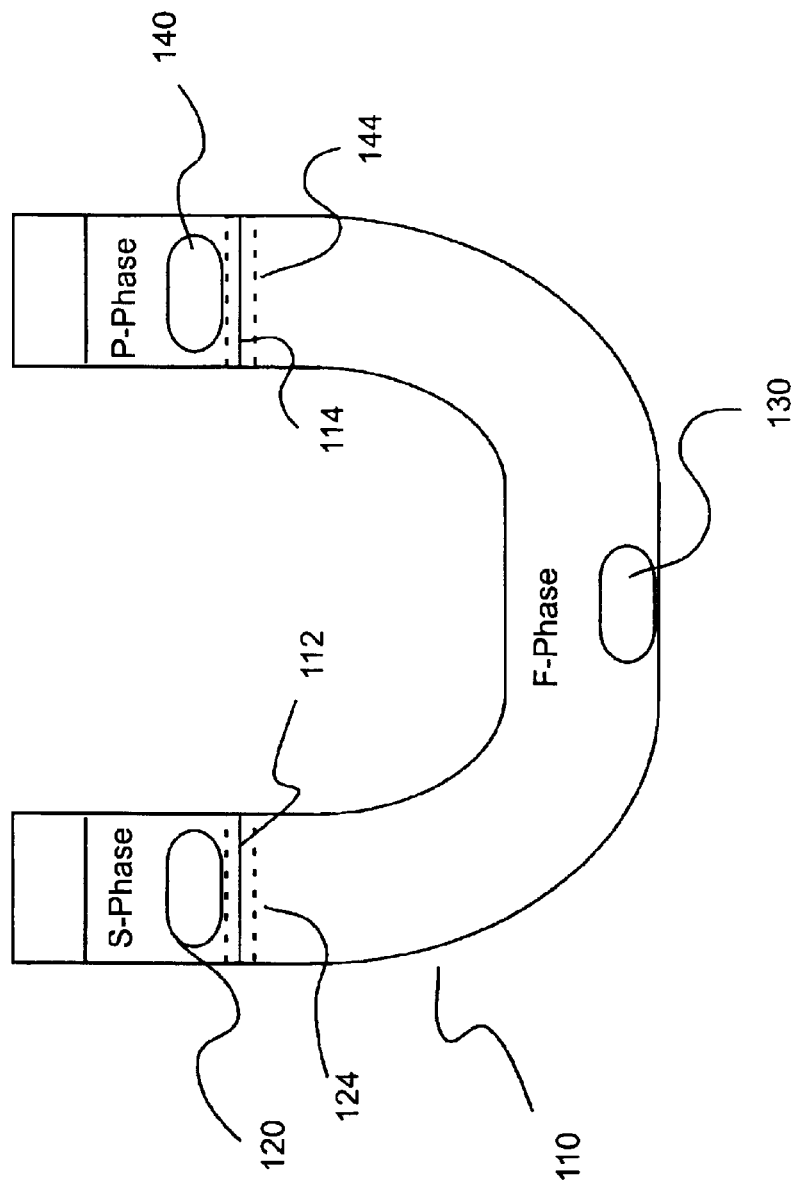
FIG. 2 illustrates another embodiment of a triphasic U-tube reaction/separation apparatus of the present invention in which stirring elements or members are positioned within each of the first organic phase, the second organic phase and the intermediate fluorous phase.

The reactions of Table I were accelerated when each phase was stirred during the reaction process using a modified U-tube reactor 110 as illustrated in FIG. 2. In FIG. 2, the S-phase was positioned in the left side of U-tube 110 and contacted the F-phase at phase interface 112. A stirring element 120 (for example, a magnetic stirring element) was positioned within the S-phase. In one embodiment, stirring element 120 was supported in the S-phase by a support (for example, a porous glass frit 124) that allowed fluid contact between the S-phase and the F-phase while supporting stirring element 120. A stirring element 130 (for example, a magnetic stirring element) was also positioned with the F-phase. The F-phase was in contact with a P-phase as described above at phase interface 114. A stirring element 140 (for example, a magnetic stirring element) was positioned within the P-phase upon a support (for example, a porous glass frit 144) that allowed fluid contact between the P-phase and the F-phase. Using the apparatus of FIG. 2, the deprotection reactions were completed in 18–20 h with $H_2SO_4$ or $H_2SiF_6$ (as opposed to 2–4 days in the apparatus of FIG. 1—that is, without stirring elements 120, 130 and 140) and 2a was obtained only in the P-phase (see entries 4 and 5 vs. 8 and 9 in Table I).

The effect of $K_P$ (generally equivalent to $K_D$ in these studies) of the substrates on the reaction was also studied (see, for example, entries 10–13 of Table 1). In general, the fluorine content of the fluorous tag (Rf) is preferably chosen such that the silyl ether is not highly fluorous, but instead divides between the fluorous and organic phases. The reaction of 1b, which contains 21 fluorine atoms and has a measured $K_P$ of approximately 2.7 (as compared to the 17 fluorine atoms and measured $K_P$ of 0.92 of 1a), required 6 days to give 2a in quantitative yield. Without restriction to any mechanism, it is believed that the longer reaction times experienced with 1b as compared to 1a arise because the increased $K_P$ as compared to 1a resulted in decreases/limited diffusion of the tagged silyl ether into the P-phase. Such prolonged reaction time can result in increased back transport of the product alcohol to the S-phase. Indeed, the final product distribution was in the ratio of 84/16 in the P- and S-phases, respectively. It was also observed that the reactions of 1c–e, which contain fewer fluorine atoms than 1a (13, 9 and 0, respectively) and have lower $K_P$s than 1a (0.39, 0.12 and 0.015, respectively), required prolonged reaction times to complete the reactions, which made the back transport of product 2a increase. The results indicate that the $K_D$ or $K_P$ in these examples ($[M]_{F\text{-}phase}/[M]_{S\text{-}phase}$) for the substrate to be used in triphasic deprotection reaction is preferably in the range of approximately 0.01 to approximately 10. More preferably, the $K_P$ for the substrates is in the range of approximately 0.1 to approximately 5. Most preferably, the $K_P$ for the substrates is in the range of approximately 0.5 to approximately 2.0.

The generality of the present invention was demonstrated in studies of fluorinated silylethers derived from various other alcohols. The silylethers 1f–h, which have an aromatic functional group in the molecules, underwent a triphasic deprotection of the present invention to give 2f–h in 87–95% yields with high P-phase selectivities. The measured $K_P$s (equivalent to $K_D$s in theses studies) of silylethers 1f–h were in the range of approximately 0.72–1.5. The reactions of the aliphatic silylethers 1i–k, having measured $K_P$s in the range of approximately 5.0–8.2, required longer reaction times (7 days or more), which once again resulted in decreased P-phase/S-phase selectivities (entries 17–19). In the case of 1j, 2j was obtained only in 38% yield after 7 days. This was probably a result of the high $K_P$ of 1j as well as its low reactivity for the deprotection reaction. Indeed, the reaction of 1j was not completed even after 2 days even in "ordinary" monophasic conditions, whereas the reaction of 1a was completed in 30 min under the same monophasic condition.

The results of the studies of the present invention indicate that the $K_D$ or $K_P$ of a substrate can be "tuned" or optimized for use in the triphasic systems of FIGS. 1 and 2 by altering the number of fluorine atoms in the molecule. For example, fluorous ether 1k with a $K_P$ of 5.7 underwent complete reaction in 7 days with a final product distribution ratio of 91/9 in P-/S-phases respectively, whereas the reaction of 11 with a $K_P$ of 1.9 completed in 1.5 days to give a product distribution ratio of 96/4 ratio in the P-/S-phases (entries 19 and 20).

The purification of a product from the reaction mixture is a very important process, particularly in large-scale organic synthesis. To illustrate this aspect, the triphasic reaction systems of the present invention provide an efficient route to separation/purification. Purificative deprotection using the triphasic reaction system of equation (2) was studied.

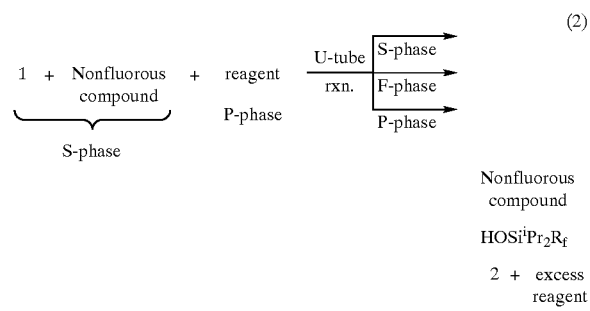

Figure 3:
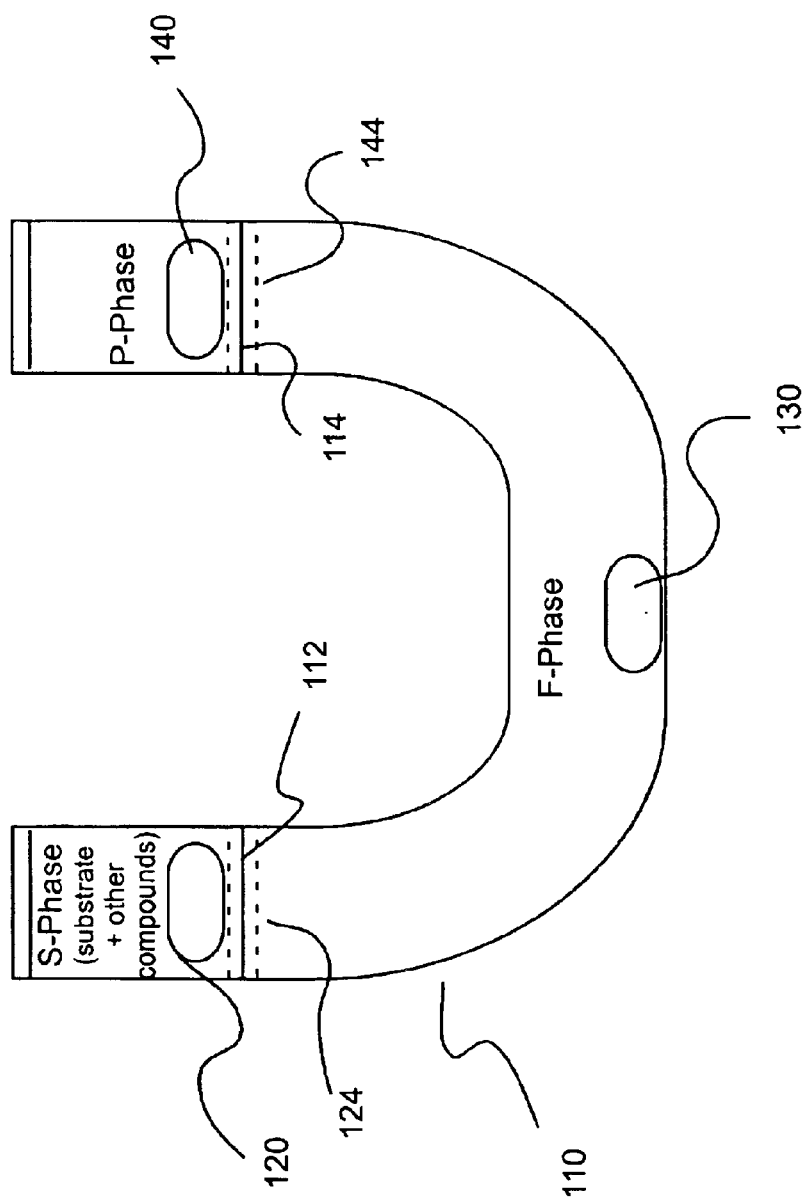
FIG. 3 illustrates an embodiment of the present invention in which one or more compounds other than the substrate compound (for example, impurities) are present in the S-phase of the triphasic system of FIG. 2.

In these studies, the fluorous-tagged compound 1a was mixed with various amounts of the unfluorinated compound, 1-(2-naphthyl)ethanol. The mixture was formed in the S-phase and subjected to the triphasic reaction/separation conditions of the present invention in which each of the S-phase, the F-phase and the P-phase was stirred as illustrated in FIGS. 2 and 3. The corresponding alcohol 2a was obtained in the P-phase free of the 1-(2-naphthyl)ethanol (see, for example, entries 1–4, in Table II). In general, the ratio of 2a in the P-and S-phases became lower as the amount of 1-(2-naphthyl)ethanol increased.

presence of (S)-(−)-2-phenylpropanol (1.0 equiv), and 2-phenylpropanol was obtained in 76% total yield in a ratio with 39/61 in P-/S-phases. The ee values of 2-phenylpropanol were 89% and 87% in P- and S-phases, respectively.

In another aspect, the present invention can be used in catalyzing or promoting the reaction between two non-fluorous (for example, organic) reaction components with a fluorous catalyst or reagent. The method provides, for example, for separation of an organic product from other undesired organic compounds (for example, unreacted starting materials or impurities in the first organic phase) as well as from the remaining catalyst or reagent and any fluorous byproducts derived therefrom. This process has advantages over previous fluorous biphasic processes, which provide for the separation of fluorous from non-fluorous components but which do not provide for the separation of any non-fluorous (for example, organic) components from any other non-fluorous (for example, organic) components.

In an illustrative example, a coupling reaction was conducted between (E)-2-bromostyrene (PhCH=CHBr) and phenylzinc iodide (PhZnI) promoted by a fluorous palladium catalyst. The catalyst was prepared from $Pd_2(dba)_3$ and the known fluorous phosphine $(p-C_6F_{13}CH_2CH_2C_6H_4)_3P$. A mixture of the catalyst in FC-72 was contacted in a U-tube with a first organic phase containing (E)-2-bromostyrene in acetonitrile and a second organic phase containing phenylzinc iodide in THF. After one day at ambient temperature, each organic phase was removed and subjected to standard aqueous workup. Unreacted (E)-2-bromostyrene was recovered from the first organic phase while the coupled reaction product, (E)-stilbene (PhCH=CHPh) was isolated from the second organic phase.

A similar control experiment was conducted but the fluorous catalyst was omitted and a standard organic catalyst $((Ph_3P)_4Pd)$ was added to the second organic phase containing the PhZnI. In this experiment, no coupled product was isolated in either organic phase, and the bromostryene was recovered from the first but not the second organic phase.

TABLE II

Purificative Deprotection from the Mixture of Fluorinated and Unfluorinated Compounds Using Triphasic Reaction System

| entry | fluorinated substrate, 1 | unfluorinated compound (equiv)[a] | time | yield of 2, (%) | ratio of 2 in P-/S-phases |
|---|---|---|---|---|---|
| 1 | 1a | 1-(2-naphthyl)ethanol (0.2) | 1 d | 87 | 99/1 |
| 2 | 1a | 1-(2-naphthyl)ethanol (0.4) | 1.5 d | 96 | 96/4 |
| 3 | 1a | 1-(2-naphthyl)ethanol (0.6) | 3 d | 97 | 95/5 |
| 4 | 1a | 1-(2-naphthyl)ethanol (1.0) | 2.5 d | 96 | 94/6 |
| 5 | 1f | (R)-(+)-1-(2-naphthyl)ethanol(1.0) | 2 d | 83[b] | 41/59(>97% ee/90% ee)[c] |
| 6 | 1m | (S)-(−)-2-phenylpropanol (1.0) | 2 d | 76[b] | 39/61(89% ee/87% ee)[c] |

[a]The equivalents are based on 1.
[b]The yields are based on the total amount of both enantiomers in the reaction.
[c]The enantiomeric purity of the corresponding alcohols obtained in each phase is shown in the parentheses. The ee values were determined by optical rotation.

Furthermore, the purificative deprotections of the chiral silylethers (1f and 1m) were examined in the presence of the corresponding enantiomerically pure alcohols using the triphasic system of FIGS. 2 and 3. The deprotection reaction of 1f (1.0 equiv) proceeded in the presence of (R)-(+)-1-(2-naphthyl)ethanol (1.0 equiv), and 1-(2-naphthyl)ethanol was obtained in 83% total yield in a ratio with 41/59 in P-/S-phases (entry 5). The enantiomeric excess (ee) values of 1-(2-naphthyl)ethanol obtained were >97% and 90% in P- and S-phases, respectively. The chiral silyl ether 1m (1.0 equiv) also underwent the purificative deprotection in the This process has advantages over both standard and fluorous biphasic coupling reactions. In the standard (non-fluorous) process where the (E)-2-bromostyrene is not consumed, it is necessary to separate the stilbene product from the catalyst and any catalyst-derived products as well as from the unreacted bromide. A fluorous biphasic process can provide for catalyst separation but results in a mixture of the stilbene product and the unreacted bromide. As shown above, the present invention also provides for separation of any other compounds, for example, impurities, from the bromide provided that these other compounds are not transported through the fluorous phase during the course of the reaction (in this case, about 1 day).

Without restriction to any mechanism, the inventors speculate that the bromide reacts over one or more steps with the fluorous palladium catalyst in the first organic phase, at the interface between the first organic phase and the fluorous phase or in the fluorous phase. This provides an organometallic intermediate or intermediates containing one or more fluorous phosphines. These phosphines facilitate transport of the intermediate(s) through the fluorous phase. The transported intermediate or intermediates then react over one or more steps with the phenylzinc iodide in the second organic phase, at the interface between the second organic phase and the fluorous phase, or in the fluorous phase but close to the interface between that phase and the second phase. The resulting product partitions favorably into the second organic phase and its rate of transport through the fluorous phase to the first organic phase is slow relative to the rate of the reaction.

As illustrated by the coupling reaction, this aspect of the present invention is especially convenient for organic reactions that are promoted by complexed metal reagents or catalysts because the complexes can be rendered fluorous either by using known fluorous ligands or by converting known or new organic ligands into fluorous ligands by adding appropriate fluorous tags, domains or ponytails. Other suitable reactions include, but are not limited to Heck reactions, Stille reactions, Sonagashira reactions and Suziki reactions.

However, the method is not limited in any way to these types or classes of reactions and can be used in substantially any non-fluorous (for example, organic, organometallic or inorganic) reaction in which a reaction component from the first non-fluorous phase or an intermediate derived from reaction or interaction of that component with the fluorous component is transported and reacted to provide a product in the second non-fluorous phase faster than that product or other components in the second non-fluorous phase are transported to the first non-fluorous phase. Ideally, none of the original components or the newly formed products of the second non-fluorous phase should be transported to the first non-fluorous phase during the course of the reaction and separation. However, in practice, zero or near zero transport rates are rare. Preferably, the majority of the original components and/or newly formed products of the second non-fluorous phase remain in that phase at the end of the reaction. More preferably, more than about 75% remain in the second phase. Most preferably, more than about 90% of the original components and/or newly formed products of the second non-fluorous phase remain in that phase at the end of the reactions.

While it is often appropriate that the reaction component in the fluorous phase is a reagent or catalyst, this is not necessary in the case where the component or components in the first non-fluorous phase and the components or components in the second non-fluorous phase undergo a reaction when contacted with each other in the second non-fluorous phase or at or near the interface between the fluorous phase and the second non-fluorous phase under the conditions of the reaction and separation. In such cases, the fluorous components serves to transport, either by reversible chemical bond formation or other reversible interaction, one or more of the components of the first non-fluorous phase to the second non-fluorous phase or to the vicinity of the interface between the fluorous phase and the second non-fluorous phase. Those skilled in the art often call molecules that are transported "guests" and molecules that effect transport "host" or "transport agents". Many non-fluorous guests and hosts are known to those skilled in the art and known or new guests or hosts can be rendered fluorous for use in the present invention by attaching suitable fluorous tags, domains or ponytails.

One example of such a transport agent that has been rendered fluorous for use in the present invention is a barbiturate receptor originally prepared by Chang and Hamilton. Chang, S. K; Hamilton, A. D., J. Am. Chem. Soc., 1988, 110, 1318. The active portion of the non-fluorous transport agent or host 3a (see FIG. 4) has 6 hydrogen bonding sites projecting to the interior of a planar cavity. These 6 hydrogen bonding sites are geometrically complementary to the barbiturate (malonylurea) structure. Drugs such as phenobarbital reversibly associate with transport agents such as 3a in a variety of solvents. See, for example, Valenta, J. N.; Sun, L.; Ren, Y.; Weber, S. G., Anal. Chem., 1997, 69, 3490. By covalent modification of the receptor with a fluorous chain (carboxy terminated perfluoropolypropylene oxide, Krytox, available from DuPont, average molecular weight 1200) 3a was rendered fluorous soluble in the form of fluorous transport agent 3b. Transport agent 3b was found to have the ability to transport barbiturates through a fluorous phase. The direction of the transport can be defined by control of the conditions in the S-phase and the P-phase. Barbiturates are weak acids, therefore transport to the P-phase is favored if the P-phase is basic. The acidic barbiturate at the F-phase/P-phase boundary can react with hydroxide ion in the P-phase to yield the more P-phase soluble barbiturate anion.

Figure 4:
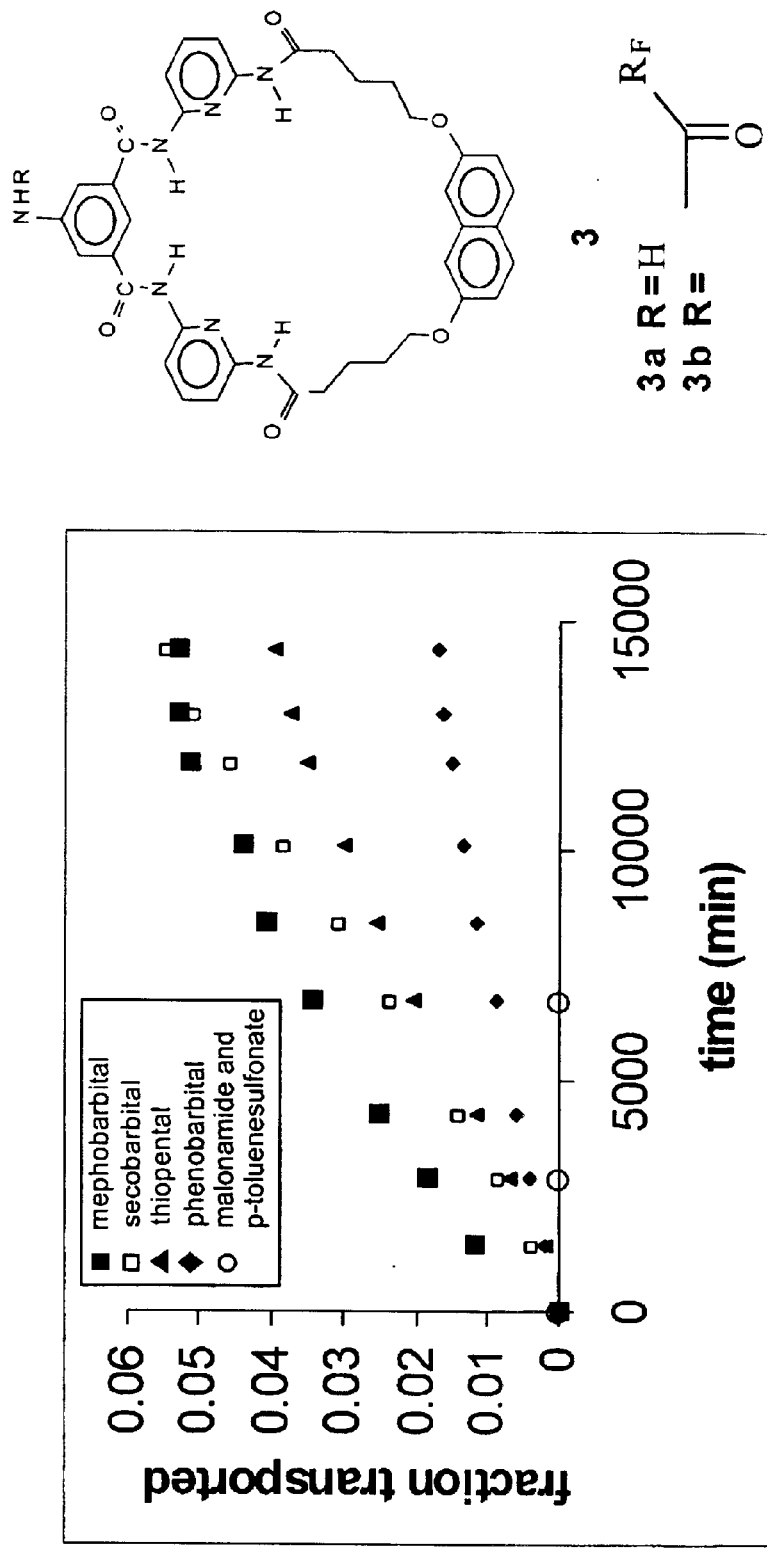
FIG. 4 illustrates studies of one embodiment of the present invention in which a fluorous receptor facilitates transport of a compound through a fluorous phase from a first aqueous phase to a second aqueous phase.

In an illustrative example, several transport experiments were carried out with a variety of guest molecules and fluorous transport agent 3b. The F-phase included transport agent 3b, at about 1 mM in the fluorous solvent FC-72. This F-phase was contacted in a U-tube with a first phase containing various organic compounds in water and a second aqueous phase containing hydroxide ion (pH 11.5 phosphate buffer). After various periods of time at ambient temperature, a portion of the more basic, P-phase was removed and subjected to quantitative analysis by UV absorbance spectrophotometry. The measured absorbances were converted to the concentration of each organic compound by the use of a calibration curve. The organic solutes tested were phenobarbital, secobarbital, mephobarbital, thiopental, 2-ethyl, 2-phenylmalonamide, and p-toluenesulfonate. FIG. 4 shows the results of these studies. The amount of each compound transported (as a fraction of the amount in the S-phase) is plotted versus time. The data points represent behavior of mephobarbital (represented by solid squares), secobarbital (represented by open squares), thiopental (represented by triangles), phenobarbital (represented by diamonds), malonamide and p-toluenesulfonate (both represented by open circles). Each of the barbiturates was transported through the fluorous phase in the presence of transport agent 3b. As expected, there was no transport of p-toluenesulfonate or 2-ethyl, 2-phenylmalonamide (which do not associate with transport agent 3b) with transport agent 3b in fluorous phase.

A control experiment was conducted with phenobarbital wherein fluorous transport agent 3b was omitted from the fluorous phase. In this experiment, no phenobarbital (the only solute tested) was transported to the P-phase.

In all of the above aspects, a chemical reaction in the second non-fluorous phase and/or at or near the vicinity of the interface between the fluorous phase and the second non-fluorous phase drives the transport of the reaction/separation system in a non-equilibrium fashion. The chemical energy of the reaction is used to drive the separation by stranding a product or products in the second non-fluorous phase. This non-equilibrium transport is advantageous since it increases the amount of purified non-fluorous component that can be obtained from the second non-fluorous phase at the end of the reaction.

In other aspect, this invention provides for equilibrium separation processes with either fluorous-tagged components or fluorous reagents or catalysts. Because separation precedes or at least is simultaneous with reaction, the combined reaction and separation processes illustrated above clearly show that "separation only" processes of the present invention are also operational and useful. As an example of a gradient-driven, separation-only process, a 1/1 mixture of the silyl ether 1g of cinnamyl alcohol and the free alcohol 2-(2-naphthyl)ethanol 1a in a first organic phase of acetonitrile was contacted with FC-72 in a U-tube. Also present was a second organic phase of acetonitrile containing no other reagent or additive. As presaged by the experiments above, over time the fluorous silyl ether was preferentially transported to the second organic phase (see data in Examples section). As a result of the more rapid transport of the fluorous-tagged component, the system approaches equilibrium in this component faster than the non-tagged component. Thus, the second organic phase is enriched in the fluorous-tagged compound relative to the first organic phase. If desired, the second organic phase containing predominantly the fluorous-tagged product can be removed and fresh solvent can be added to increase the gradient. The process continues until such point as the concentration of the fluorous tagged component decreases in the first organic phase to the point where transport of the organic product becomes competitive.

While the methods and apparatuses of this invention can be used to advantage in a stand alone fashion in many reaction and/or separation processes, another useful aspect of the current invention is that these methods and apparatuses can be combined in a modular fashion to make sequential or simultaneous, multi-step reaction and/or separation processes.

Figure 5:
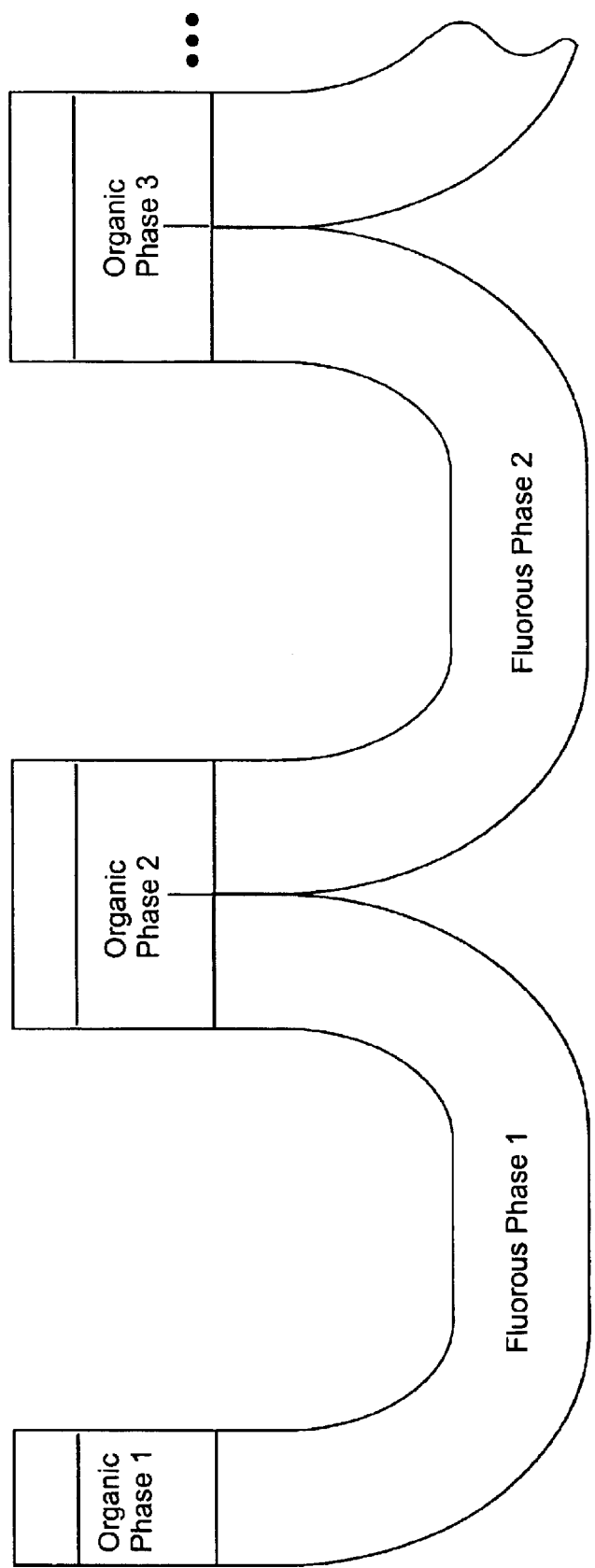
FIG. 5 illustrates an embodiment of the present invention in which a plurality of triphasic systems of the present invention are connected in series.

For example, detagging and metal catalyzed coupling reaction and separation processes can be conducted together in a "double U-tube" apparatus like that shown in FIG. 5. A substrate containing a fluorous tag and a functional group, for example a halide, for metal coupling is placed in a first organic phase which is contacted with a first fluorous phase containing only FC-72. This substrate may contain impurities which, for example, do not have either or both the fluorous tag and/or the functional group need for coupling. The first fluorous phase contacts a second organic phase containing the detagging reagent. The second organic phase also contacts a second fluorous phase containing a fluorous metal catalyst such as, for example, the palladium catalyst described above. In this embodiment, the apparatus is designed such that the second organic phase contacts both the first and second fluorous phases, but the first and second fluorous phase do not contact each other. The second fluorous phase also contacts a third organic phase containing an organic reagent or reactant, for example a zinc reagent like that shown above, that participates in the coupling but that is not rapidly transported out of the third organic phase.

Over the course of the reaction/separation, the fluorous-tagged substrate migrates through the first fluorous phase and detagging occurs to provide a product containing the coupling functionality in the second organic phase. The low partition coefficient of this non-fluorous product retards back transport to the first phase and instead the fluorous catalyst in the second fluorous phase transports the product towards the third organic phase, whereupon metal-catalyzed coupling with the reagent therein occurs. The final detaged, coupled product is then isolated from the third organic phase, largely free from the residual fluorous tag (which partitions between the two fluorous phases), the catalyst (in the second fluorous phase), and the original impurities (if any). In this way, multistep reaction and separation processes can be conducted concurrently.

Figure 6:
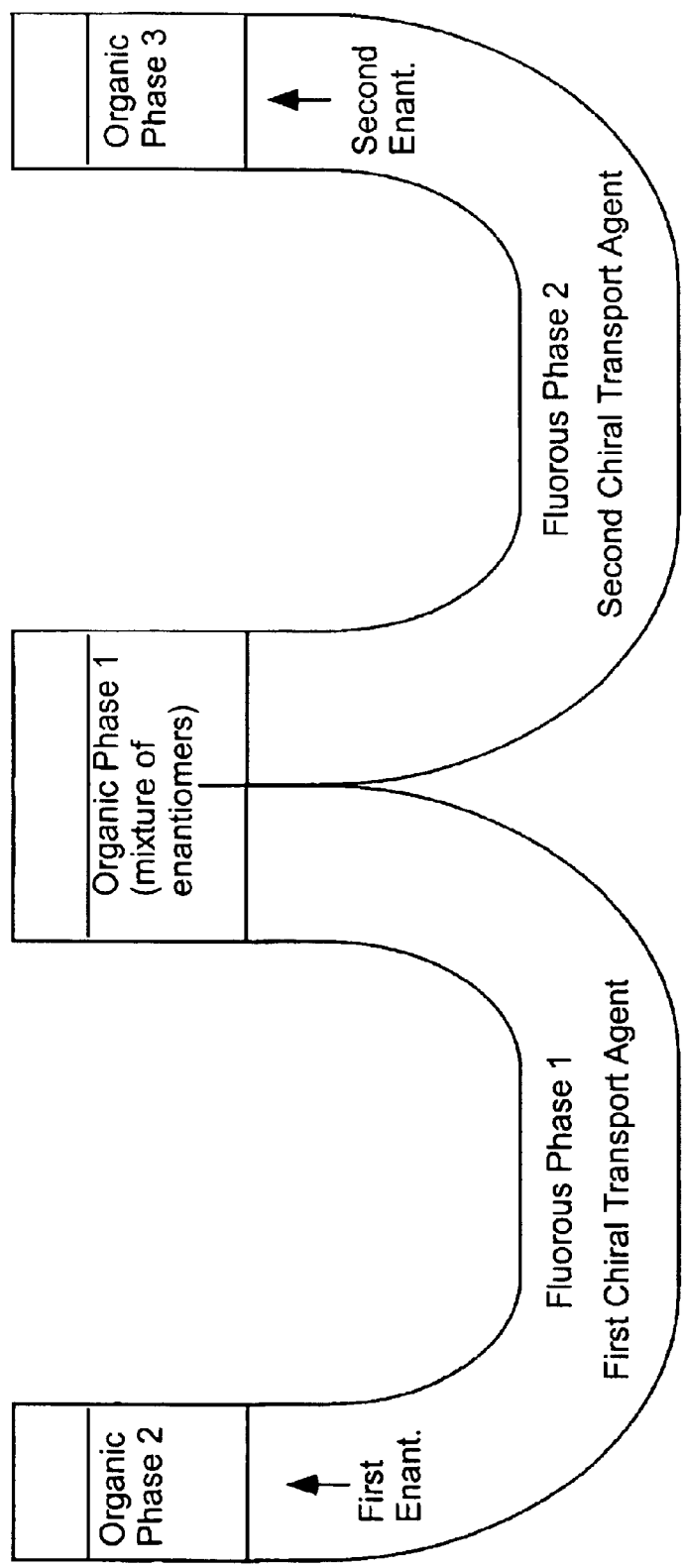
FIG. 6 illustrates another embodiment of the present invention in which a plurality of triphasic systems of the present invention are connected.

The reaction and/or separation process can also be conducted starting from the center of the apparatus, as shown in FIG. 6. Among many possible systems to separate two or more compounds with or without associated reactions, FIG. 6 illustrates the transport of two enantiomers with chiral hosts driven by a gradient. In this experiment, the first organic phase containing a mixture of enantiomers is contacted with the a first fluorous phase containing a chiral transport agent that selectively transports one of the enantiomers and a second fluorous phase containing a second chiral transport agent (often, but not necessarily, the enantiomer of the first) that selectively transports the other enantiomer. The enantiomers are then resolved in a parallel process that transports one to the second organic phase and the other to the third organic phase. As noted above, the second and third organic phases can be periodically removed and replaced by fresh solvent to maintain a gradient. Alternatively, a reagent can be added to the second organic phase and/or to the third organic phase to promote a reaction that retards the back transport of the resulting product.

In processes containing more than one fluorous liquid phase, the distribution coefficients of any fluorous component may need to be higher than in processes that have only one fluorous phase. For example, the efficiency of the parallel resolution in FIG. 6 decreases if the fluorous transport agent in the first fluorous phase can be transported through the first organic phase to the second fluorous phase and/or if the agent in the second fluorous phase is transported to the first fluorous phase. To prevent this cross-contamination, it is preferable that fluorous catalysts, reagents or transport agents in processes with more than one fluorous liquid phase have distribution coefficients (as measured between the respective fluorous phase and organic phase 1) more than about 10. More preferably, these distribution coefficients are more than about 50, and, most preferably, they are more than about 100

Figure 7B:
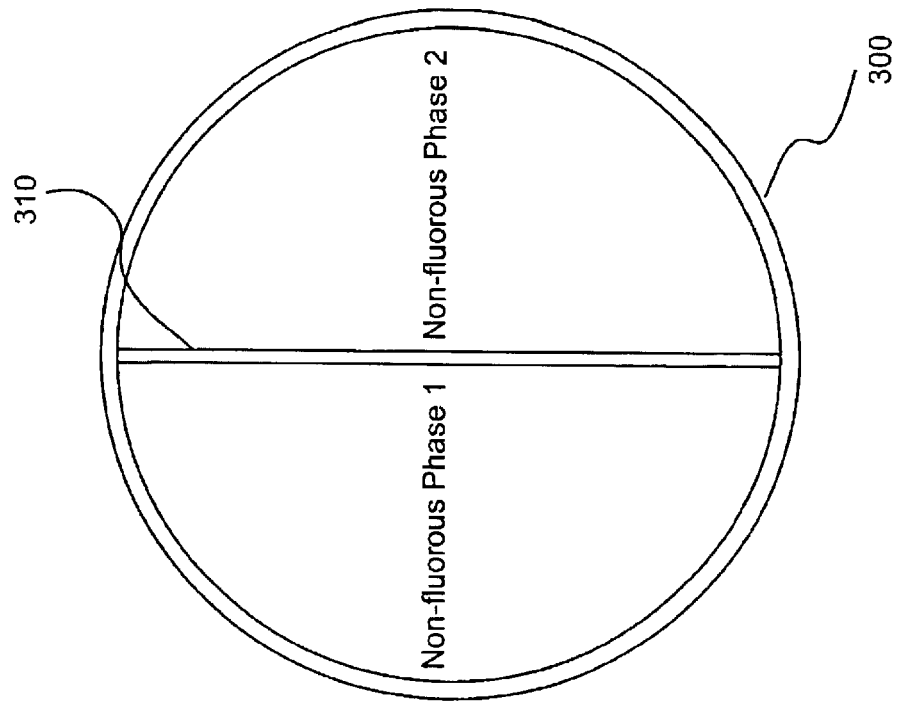
FIG. 7B illustrates a top plan view of the system of FIG. 6A.
Figure 7A:
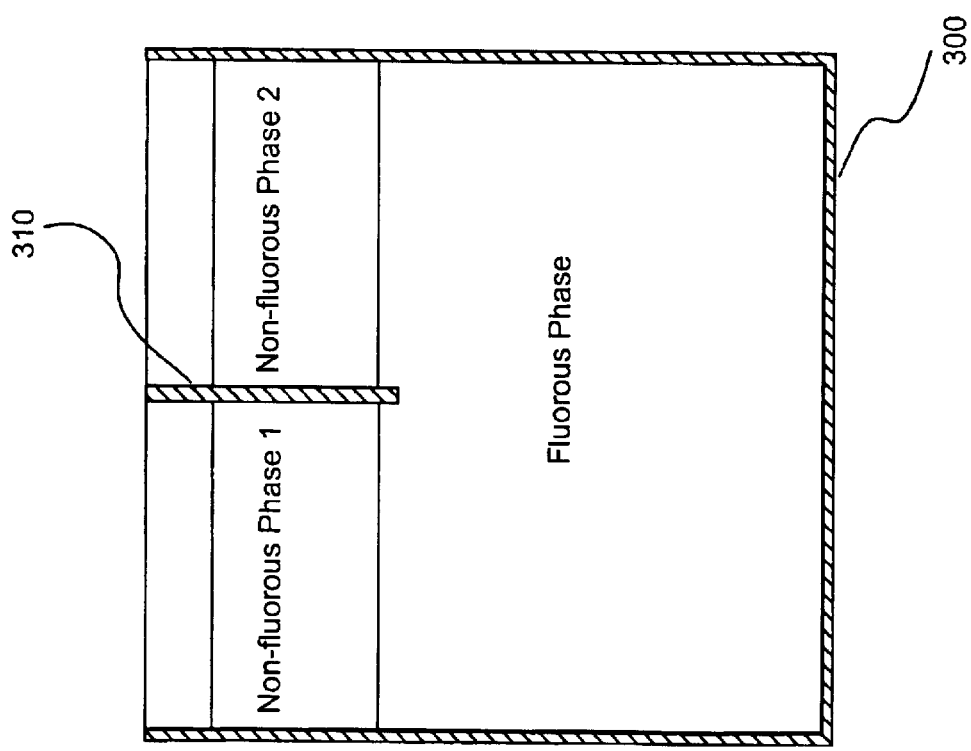
FIG. 7A illustrates a side, cross-sectional view of a multiphase system of the present invention.

As illustrated in the above examples, a simple "U-tube" is a convenient apparatus for many of the reactions and/or separations of the present invention. However, the present invention is not restricted to this type of physical apparatus and many other designs are possible. For example, as illustrated in FIGS. 7A and 7B, dividing the upper part of a, for example, cylindrical reaction vessel 300 into two parts with a suitable divider 310 provides for a fluorous phase on the bottom of the apparatus with a first non-fluorous phase on one side and a second non-fluorous phase on the other side. Divider 310 prevents contact of the first and second non-fluorous phases as well as preventing contact of the first and second fluorous/non-fluorous phase interfaces.

Figure 8B:
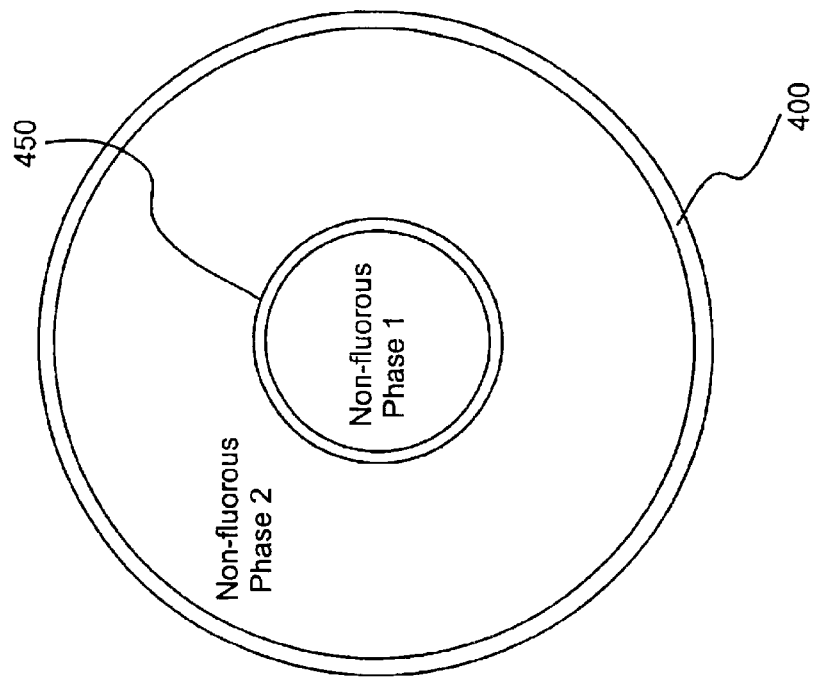
FIG. 8B illustrates a top plan view of the system of FIG. 7A.
Figure 8A:
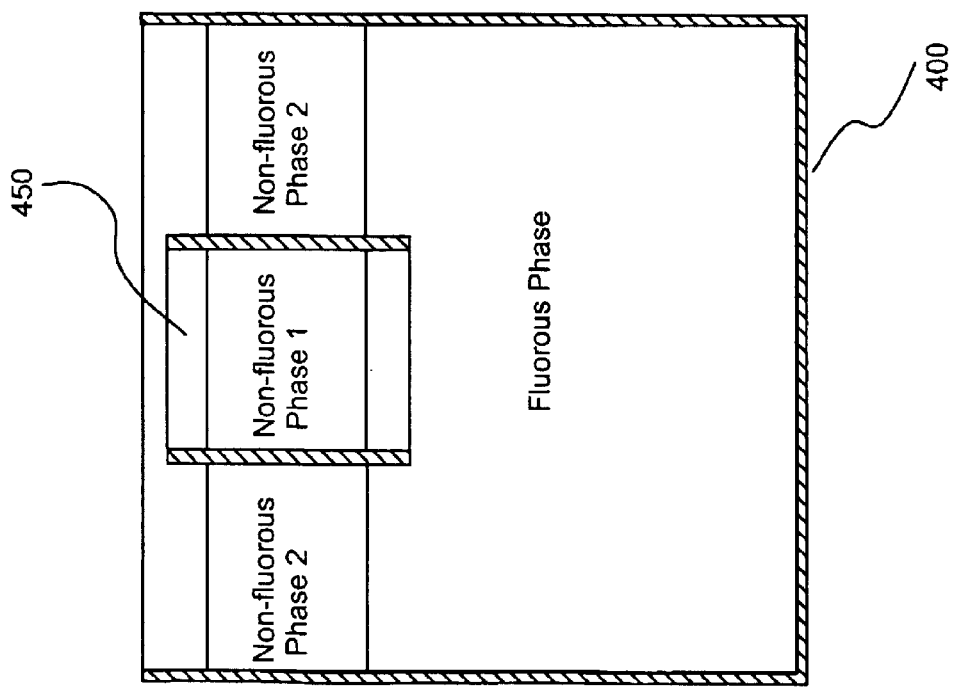
FIG. 8A illustrates a side, cross-sectional view of another multiphase system of the present invention.

Likewise, as illustrated in FIGS. 8A and 8B, immersion of an open-ended container 450 of substantially any shape (cylindrical, square, rectangular, irregular) into the upper part of a reaction vessel 400 provides for a fluorous phase on the bottom with a first non-fluorous phase on the inside or outside of open-ended container 450 and a second non-fluorous phase on the opposite side of open-ended container 450 from the first non-fluorous phase. For example, the first non-fluorous phase could be on the inside of open-ended container 450 and the second phase on the outside of open ended container 450. In general, substantially any apparatus or vessel can be used provided that it prevents direct contact between the two non-fluorous phases and it also prevents contact of the interface of the first non-fluorous phase and the fluorous phase with the interface of the second non-fluorous phase and the fluorous phase.

On rare occasions, the density of one or both of the non-fluorous phases may be higher than that of the fluorous phase. In the case where both non-fluorous phases are more dense than the fluorous phase, inverted variants of the apparatuses shown in, for example, FIGS. 5 through 8B can be used. In the case where only one of the layers is more dense, the three phases can simply be layered one on top of the other in order of density without any special dividers.

In the examples described above, at least one of the components added to or generated in one non-fluorous phase (for example, a substrate, a product, an impurity, a reagent, a reactant, a catalyst or a scavenger) bears a fluorous group or tag, and this fluorous component, fluorous intermediates derived therefrom or fluorous product passes through the fluorous phase from one non-fluorous phase to another non-fluorous phase. The methods and devices of the present invention can thus be used for separation of organic molecules and fluorous molecules or for a combination of separation and reaction as described above.

However, the fluorous multiphasic separations and reactions of the present invention can also be conducted without using any fluorous reaction component. A fluorous phase is still used to separate two other non-fluorous (often organic or inorganic) phases that would typically be miscible or at least in direct contact in current methods. The fluorous phase regulates or controls the exchange of components in the non-fluorous phases. Generally, the fluorous phase allows a non-fluorous component (or components) originating in one of the non-fluorous phases to pass selectively into and/or through the fluorous phase as a result of its (their) distribution coefficient as described above. Components in the other non-fluorous phase do not pass into and/or through the fluorous phase (or pass into and/or through the fluorous phase very slowly) as a result of their lower distribution coefficient (insolubility or low solubility in the fluorous phase) under the conditions of the experiment as also described above.

Figure 9:
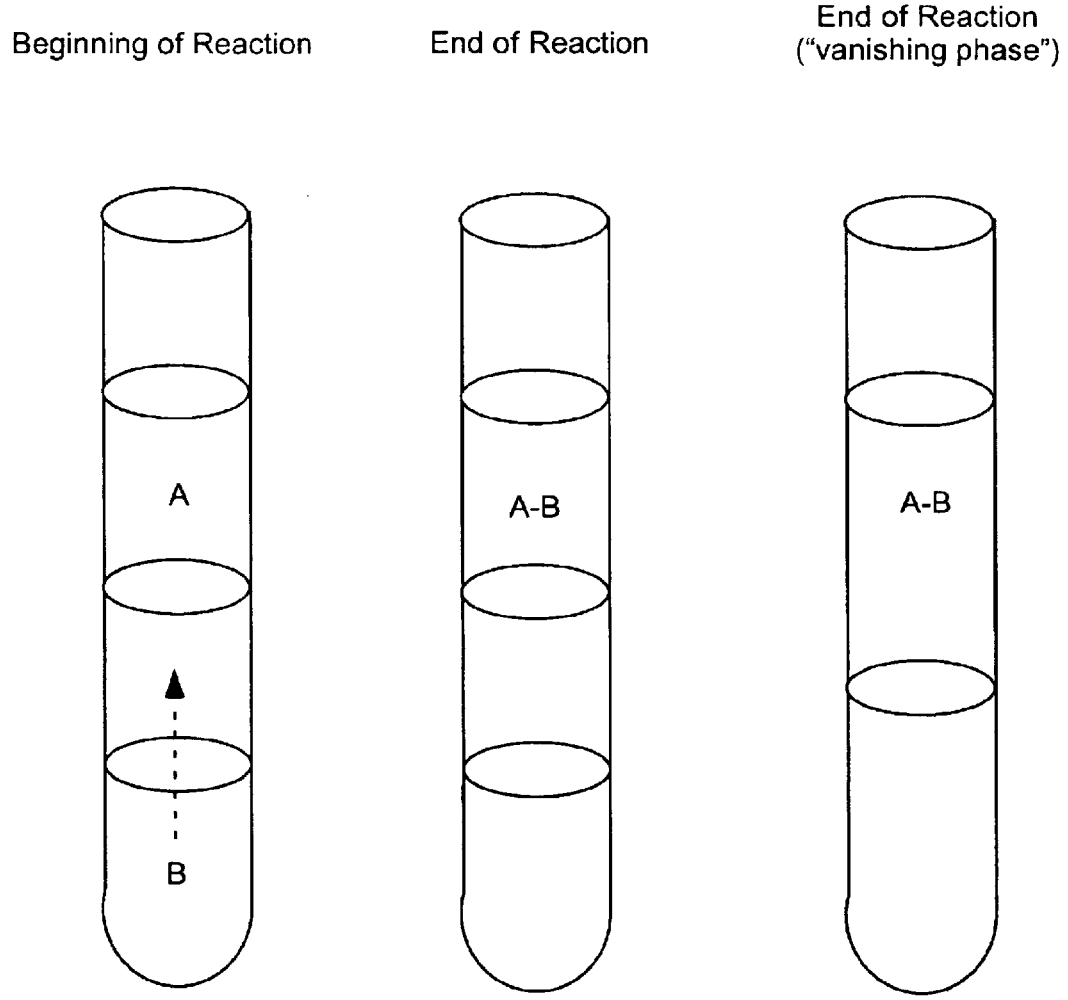
FIG. 9 illustrates another embodiment of a triphasic reaction of the present invention in which a non-fluorous reaction component transports through the fluorous phase.

In one embodiment of the present invention, a triphasic reaction occurs in which the fluorous phase is a fluorous liquid phase, one of the non-fluorous phases is liquid phase less dense than the fluorous liquid phase and the other non-fluorous phase is a liquid or solid phase more dense than the fluorous phase. FIG. 9, for example, illustrates an addition reaction of two reaction components, A and B, to synthesize a new product A–B. In this embodiment, reaction component B is transported through the fluorous phase much faster than the reaction component A.

The densities of many fluorous liquids are in the range of approximately 1.5 to approximately 2.0 g/mL (for example, perfluorohexane, 1.669; perfluoroheptane, 1.745, perfluorodecalin, 1.908). The first (less dense) non-fluorous phase can include, for example, an organic solvent or solvent mixture, or an aqueous solvent or solvent mixture containing the reaction component A, which has little or no solubility in the fluorous phase. Nearly all common organic and aqueous solvents and solvent mixtures are less dense than fluorous solvents. In some cases, no added solvent may be needed, and A (either alone or with another reaction component (or components)) can serve as the less-dense non-fluorous phase. The second (more dense) non-fluorous phase can, for example, include an organic liquid or solid phase or and inorganic liquid or solid phase that is immiscible in and more dense than the fluorous phase. Examples of organic compounds include, but are not limited to, iodomethane, iodoethane, diiodomethane, triiodomethane, tetraiodomethane, dibromomethane, tribromomethane and tetrabromomethane, iodobenzene, iodoanisoles, 3-iodobenzyl alcohol, 2-iodophenol, 2-iodothiophene, etc. Examples of inorganic compound include, but are not limited to, dibromine, diiodine, tin tetrachloride, tin tetrabromide, tin tetraiodide, titanium tetrachloride, boron tribromide, phosphorous tribromide, phosphorous oxybromide, thionyl bromide, etc. The densities of many organic and inorganic compounds are known and densities can easily be measured by standard experiments. The more dense non-fluorous phase also contains reaction component B. Indeed, in many embodiments, the more dense phase includes exclusively or primarily reaction component B.

As described above, an important feature of this and all triphasic reaction and/separation designs of the present invention is the relative rate of transport of the components (for example, components A and B in FIG. 9) from one non-fluorous phase through the fluorous phase to the other non-fluorous phase. At least one of the components (for example, component B in FIG. 9) is transported through the non-fluorous phase under the conditions of the experiment or procedure much faster than at least one other component (for example, A in FIG. 9). Preferably, the faster transported component(s) transports at a rate at least two times greater than the slower component(s). More preferably, the rate is at least S times greater. Even more preferably, the rate is at least 10 times greater, and most preferably the rate is at least 25 times greater. It is also preferable that the product of the reaction (A–B in FIG. 9) is not transported through the fluorous phase rapidly during th e course of the reaction. Preferably, less than 25% of a product or products is transported through the fluorous phase during the reaction. More preferably, less than 10% of the product is transported through the fluorous phase, and, even more preferably, less than 5% of the product is transported through the fluorous phase.

Rates of transport of non-fluorous components can readily be measured by standard experiments. In general, the component of interest is added to one non-fluorous phase of a triphasic reaction apparatus under conditions similar to the reaction conditions but without some or all of the other reagents or reactants, and its appearance in the other non-fluorous phase is measured as a function of time. However, in many cases, the measurement of transport rates is not necessary as a result of the widely differing solubilities of the reaction components. Many embodiments of this invention involve, for example, a reaction of a relatively large (for example, having a molecular weight MW preferably greater than 100, more preferably, greater than 150 and most preferably, greater than 200) and/or polar organic molecule (s). It is well known that most such molecules have little or no solubility in fluorous solvents, so the transport rate of such reaction components will be very slow (or even approaching zero) over the course of the experiments. Such components are effectively "immobilized" in their non-fluorous phase. Types of non-fluorous molecules that transport more rapidly through the fluorous phase are often small and/or highly chlorinated, brominated and/or iodinated organic or inorganic molecules. Both absolute solubilities and relative solubilities (partition or distribution coefficients) are readily measured by standard experiments, and many are already known.

To conduct the triphasic reaction and separation illustrated in FIG. 9, the three phases are carefully combined such that the two non-fluorous phases are not allowed to directly mix. For example, the phases can be added to a reaction vessel in order of decreasing density. Alternatively, the more dense non-fluorous phase is added to the fluorous phase and allowed to sink prior to adding the less dense non-fluorous phase. The phases are allowed to stand, or can be agitated or stirred gently provided that the two non-fluorous phases preferably do not mix or come into direct contact. In the example in FIG. 9, the more rapidly transported reagent B moves through the fluorous phase to react with reaction component A to form product A–B. As stated above, the product does not transport rapidly though the fluorous phase, so it resides predominately or exclusively in the same non-fluorous phase as A (in this case, the less dense non-fluorous phase). The reaction between A and B may occur in the less dense non-fluorous phase or at the interface between this phase and the fluorous phase or even in the fluorous phase near the interface, provided that the product A–B ultimately and predominantly resides in the less dense non-fluorous phase.

In cases where the more rapidly transported component is in the less dense phase and the less rapidly transported component is in the more dense phase, the product will accumulate in the bottom (more dense) phase.

Figure 10A:
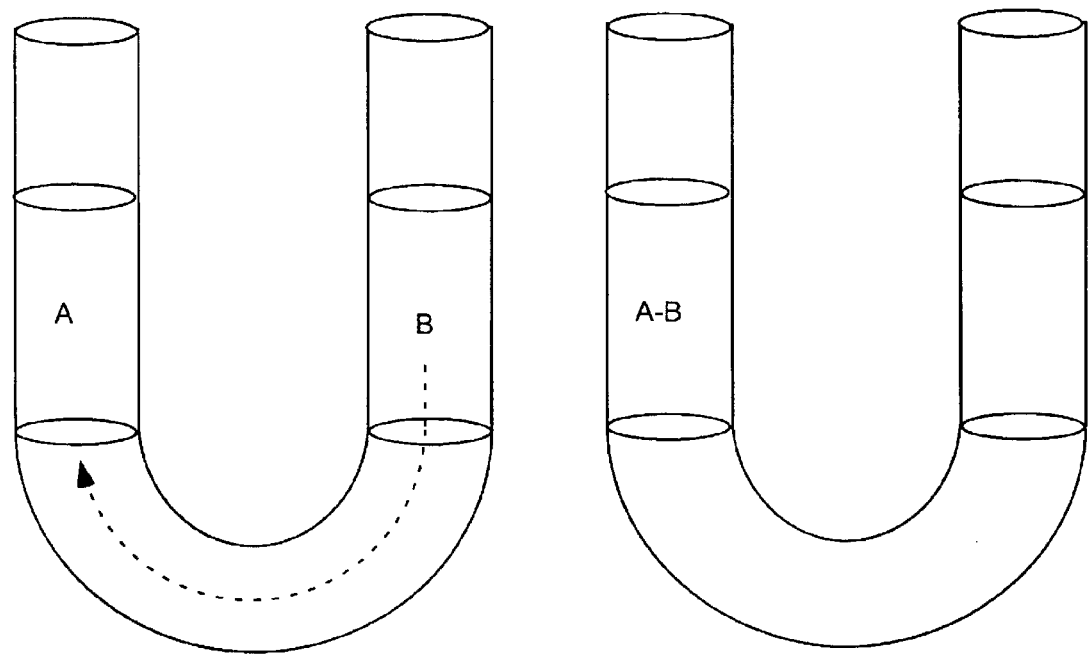
FIG. 10a illustrates an embodiment of a triphasic reaction of the present invention in a U-tube in which a non-fluorous reaction component transports through the fluorous phase.
Figure 10B:
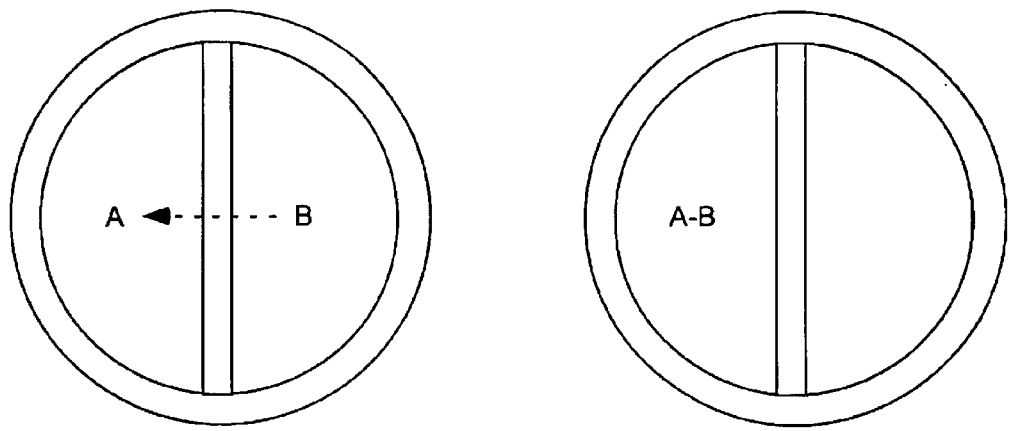
FIG. 10b illustrates an embodiment of a triphasic reaction of the present invention in which a non-fluorous reaction component transports through a fluorous membrane.

Other embodiments of this invention are shown in FIGS. 10a and 10b. FIG. 10a illustrates an embodiment of the present invention wherein the fluorous phase is a fluorous liquid and both of the non-fluorous phases are liquid phases that are less dense than the fluorous liquid phase. Features of the phases and reaction components are substantially as described above. Reaction components A and B are again transported more slowly and more quickly, respectively, and the product A–B forms on the non-fluorous side of A. FIG. 10b illustrates an embodiment of the present invention wherein both non-fluorous phases are liquid phases as described above, and the fluorous phase is a non-fluid phase such as a fluorous polymer or a fluorous membrane. An advantage of this embodiment is that the densities of the two non-fluorous phases are not important.

In the case wherein one of the non-fluorous phases contains mostly or exclusively the rapidly transported reaction component (for example, component B in FIGS. 9 through 11) and when that reaction component is not used in large excess, that non-fluorous phase may vanish during the course of the reaction (as a result of the consumption of B) leaving a final reaction mixture that has the other non-fluorous phase and the fluorous phase. Such an embodiment (sometimes referred to as a "vanishing phase" embodiment) is illustrated, for example, on the right side of FIG. 9 and in FIG. 12.

Figure 11:
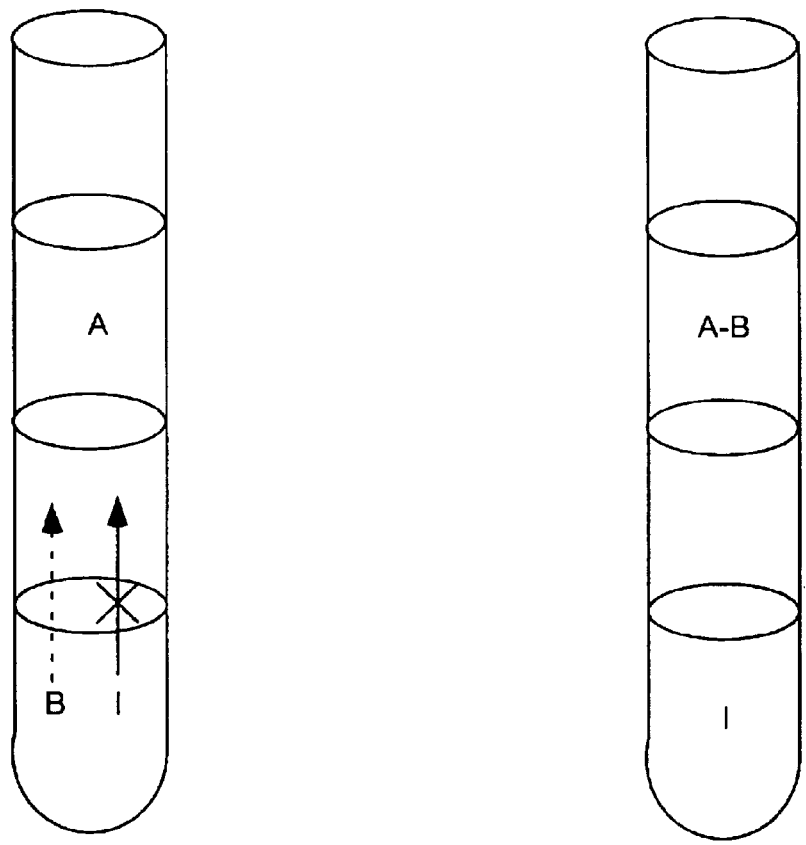
FIG. 11 illustrates separation of impurities from a transported non-fluorous reaction component in the embodiment of FIG. 9.
Figure 12:
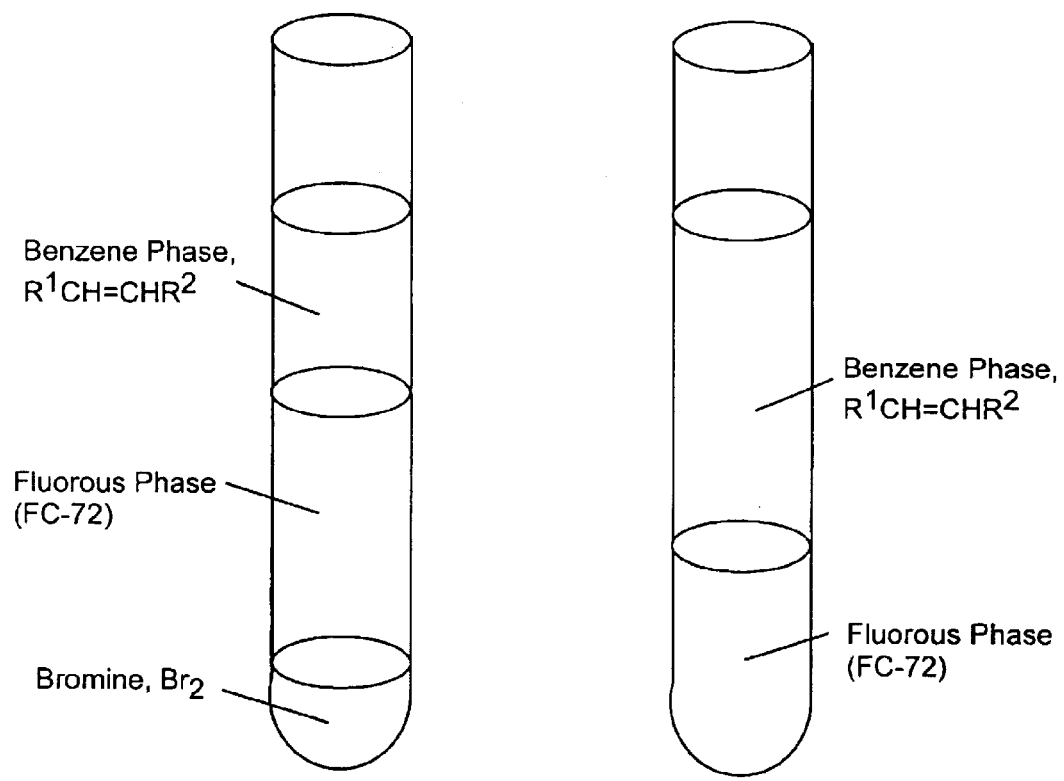
FIG. 12 illustrates an embodiment of a triphasic bromination reaction of the present invention with "phase vanishing."

The embodiments in FIGS. 9 through 11 are exemplified with a generic addition reaction (A+B→A–B) solely for simplicity and convenience. Substantially any type of organic, organometallic or inorganic reaction can be conducted provided that at least two reaction components are needed and that the components and phases of the reaction meet the specifications outlined herein. Other broad classes of reactions suitable for use in the present invention include, but are not limited to, substitutions, cycloadditions, rearrangements and fragmentations.

The novel fluorous triphasic reactions of the present invention have a number of advantages over traditional reactions that lack the fluorous phase. In traditional reactions, there is often only one phase with all the reaction components therein. Even if more than one phase is used, these phases are typically in direct contact and exchange of components depends on the nixing, the reaction rates and the relative solubilities (partition or distribution coefficients) in the two non-fluorous phases.

The novel triphasic reactions of the present invention are useful, for example, as alternatives to traditional reactions where one of the reaction components must be added slowly to another. In small scale reactions, this is often needed to regulate the relative rates of competing reactions of different reaction order (for example, competing uni- and bimolecular reactions). On large scale, slow additions are even more common since many reactions are exothermic and the evolution of heat must be controlled by regulating the reaction rate. Such reactions can require expensive equipment to effect the needed slow addition. Alternatives to slow addition are high dilution and/or cooling. The triphasic reactions described herein accomplish the same effect without complicated apparatus. The rate of the reaction is limited by the rate of transport of one of the reaction components through the fluorous phase. The reactions of the present invention are also efficient because they do not require large amount of solvents or expensive cooling.

Another advantage is that the reactions of the present invention can be used to effect a simultaneous purification. For example, if the more rapidly transported non-fluorous reaction component B contains impurities I (for example, organic or inorganic impurities) that are not rapidly transported through the fluorous phase, then impurities I will remain in the phase of origin during the reaction as illustrated in FIG. 11. Such a reaction scheme saves the time and cost associated with purifying the reagent before the reaction or the product after reaction.

Representative examples of embodiments of the present invention include reactions of appropriate organic compounds in one non-fluorous phase with dibromine (hereafter simply called bromine), diiodomethane, and tin tetrachloride in the other non-fluorous phase.

Bromination of alkenes, for example, is a typical exothermic reaction that requires control of addition rate and temperature (See, for example, *Org. Syn. Coll. Vol.* 1, 521 (1941) and *Org. Syn. Coll. Vol.* 2, 171 (1943)). These reactions are thought to occur through the intermediacy of bromonium ions, and anti addition of the two bromines is generally favored. Bromination proceeds smoothly under triphasic conditions, including an upper organic layer containing an alkene, a middle fluorous liquid phase, and a bottom bromine layer (since bromine has higher density than typical fluorous solvents (bromine: d=3.12, perfluorohexane: d=1.67)). In the representative reaction of FIG. 12, for example, bromine migrates towards the upper organic phase and reacts with the alkene ($R^1CH=CHR^2$) to give the corresponding dibromide product in the organic phase (for example, a benzene phase). Completion of the reaction is evidenced by the disappearance of the bromine phase. As described above, this triphasic reaction system is sometimes called a vanishing phase method and the features thereof resemble the features described in FIG. 9.

In a typical "phase vanishing" reaction, bromine (4.3 mmol) was added slowly to FC-72 (1.5 mL) in a test tube and then an alkene (4.6 mmol) in hexane (1.5 mL) was added on top of the FC-72. The test tube was covered with aluminum foil and kept at room temperature. After 3 days, the lower bromine layer had disappeared and the (original) middle fluorous and upper organic layers remained. The organic layer was decanted, washed with aqueous $Na_2S_2O_3$, dried over $MgSO_4$, and concentrated. Purification by a short column chromatography on silica gel with hexane gave the corresponding bromination product.

Members of a series of representative alkenes were converted to dibromides by this procedure and the results are shown in Table III. Cyclohexane underwent bromination to give trans-1,2-dibromocyclohexane in 83% yield (entry 1). The use of water and acetonitrile in place of FC-72 for the middle phase instead of FC-72 afforded trans-1,2-dibromocyclohexane in poor yields (3% and 32%, respectively). Slow stirring of a bromine layer without mixing the three phases in the test tube accelerated the reaction rate, giving trans-1,2-dibromocyclohexane in 88% yield (entry 2). Without shielding the reaction from light, cyclohexyl bromide was generated in 36% yield along with trans-1,2-dibromocyclohexane in 60% yield (entry 3). Cyclic alkenes (entries 4 and 5) and normal aliphatic alkenes (entries 6–8) underwent bromination to give the corresponding dibromides in high yields. The reactions of conjugated olefins such as styrene and ethyl acrylate also proceeded and (1,2-dibromoethyl)benzene and ethyl 2,3-dibromopropionate were obtained in 97% and 68% yields, respectively (entries 9 and 10).

TABLE III

Triphasic Bromination of Alkenes Using the Phase-Vanishing Method.

| entry | alkene | yield of dibromide (%)[a] |
|---|---|---|
| 1 | cyclohexene | 83 |
| 2[b] | cyclohexene | 88 |
| 3[c] | cyclohexene | 60 |
| 4 | cyclopentene | 79 |
| 5 | cycloheptene | 97 |
| 6 | 1-octene | 97 |
| 7 | trans-2-octene | 88 (1.8/1)[d] |
| 8 | cis-2-octene | 89 (1/24)[d] |
| 9 | styrene | 97 |
| 10 | ethyl acrylate | 68 |

[a]The yields are based on bromine.
[b]Slow stirring of a bromine layer without mixing the three phases in the test tube.
[c]The reaction was carried out without shielding from light.
[d]The number in parenthesis is the ratio of 2R*,3R* to 2R*,3S* isomers.

Figure 13:
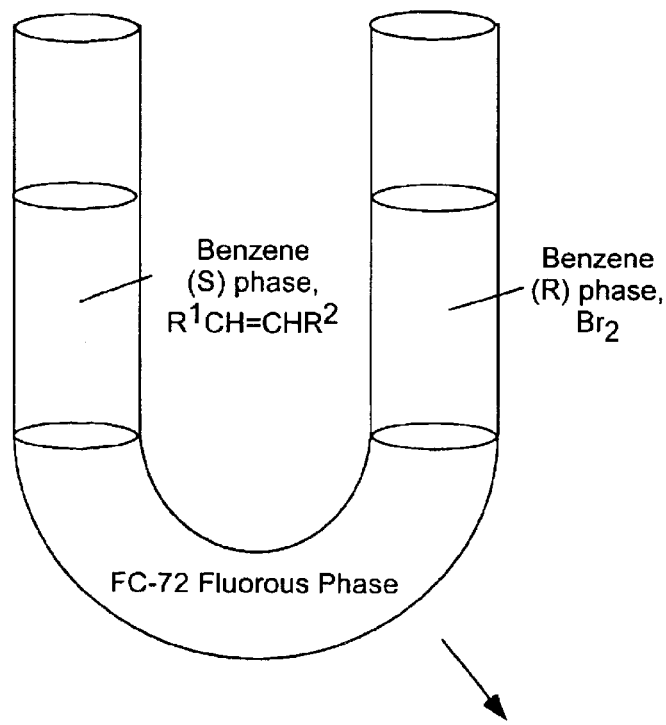
FIG. 13 illustrates a triphasic bromination reaction of the present invention in a U-Tube.
Figure 13:
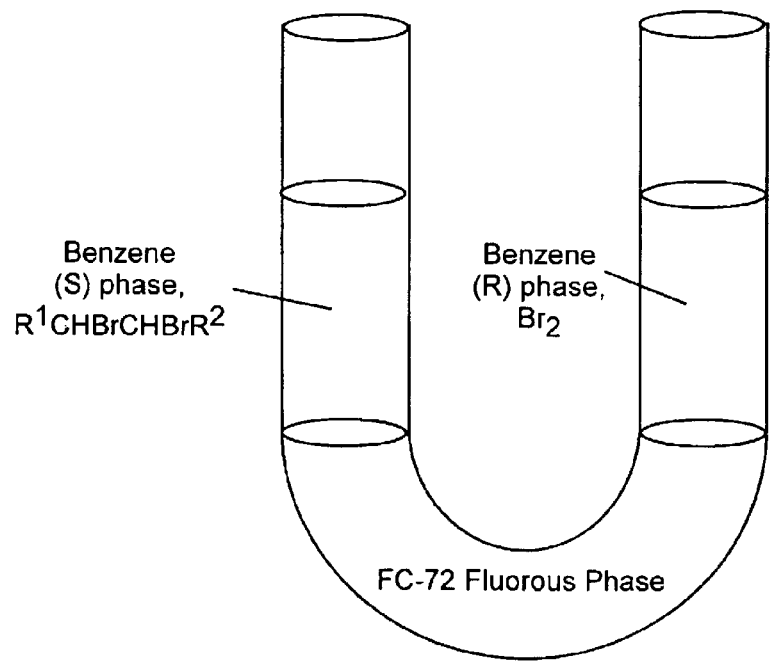

When bromine is diluted with organic solvents, the resulting solution becomes less dense than typical fluorous solvents, and the experimental or reaction setup can, for example, resemble that of FIG. 10a. In several studies, bromine and an alkene were dissolved separately in benzene, and the resulting solutions were placed in opposite sides of a U-tube bridged by FC-72 (FIG. 13). In FIG. 13, the phase containing the alkene (that is, a compound including at least one double bond and, for example, having the general formula $R^1CH{=}CHR^2$) is called the "S-Phase" (for substrate) and the phase containing the bromine is called the "R-phase" (for reactant). The product forms predominately in the S-Phase.

Members of a series of alkenes were again brominated with the results shown in Table IV. The bromination of styrene proceeded very smoothly in benzene as an organic-phase solvent and (1,2-dibromoethyl)benzene was obtained from the S-phase in 95% yield (entry 1). The reaction using $CH_2Cl_2$ for an organic-phase solvent gave (1,2-dibromoethyl)benzene in 82% yield in the S-phase, and the dibromide was also obtained from the R-phase in 12% yield (entry 2). Aromatic alkenes (entries 3–5) and aliphatic alkenes such as 5-hexenenitrile and trans-3-pentenenitrile (entries 6 and 7) underwent bromination in benzene to afford the corresponding dibromides in high yields. In the case of cyclohexane, trans-1,2-dibromohexene was obtained in 88% yield along with a trace amount of polybromination products. It is known that the polybromination of cyclohexene proceeds via a radical process under dilute conditions. See, for example, McMillen, D. W.; Grutzner, J. B. *J. Org. Chem.* 1994, 59, 4516.

TABLE IV

Bromination of Alkenes Using the U-tube Triphasic Reaction System

| entry | alkene | yield of dibromide (%)[b] |
|---|---|---|
| 1 | styrene | 95 |
| 2[c] | styrene | 82[d] |
| 3 | 2-vinylnaphthalene | 90 |
| 4 | 4-vinylbiphenyl | 96 |
| 5 | 4-phanyl-1-butene | 95 |
| 6 | 5-hexenenitrile | 93 |
| 7 | trans-3-pentenenitrile | 98 |
| 8 | cyclohexene | 88[e] |

[a]The representative procedure for styrene using the U-tube reactor is as follows. A solution of styrene (52 mg, 0.5 mmol) in benzene (2 ml) was put into one side (S-phase) of the U-tube, in which FC-72 (10 ml; F-phase) was placed, and a solution of $Br_2$ (50 μl, 1.0 mmol) in benzene (1 ml) was put into the other side (R-phase) of the U-tube. The U-tube reactor was covered with aluminum foil in order to shield it from light. The F-phase was stirred at room temperature until the color of S-phase became red. After 19 h, the S-phase was decanted and poured into aqueous $Na_2S_2O_3$ solution. The mixture was extracted with ether, washed with saturated NaCl aqueous solution, and concentrated to give pure 1,2-dibromoethylbenzene.
[b]The yields are based on an alkene.
[c]$CH_2Cl_2$ was used in the S- and R-phases.
[d]The dibromide was also obtained from the R-phase in 12% yield.
[e]Excess of $Br_2$ (8 equiv) was used.

Figure 14:
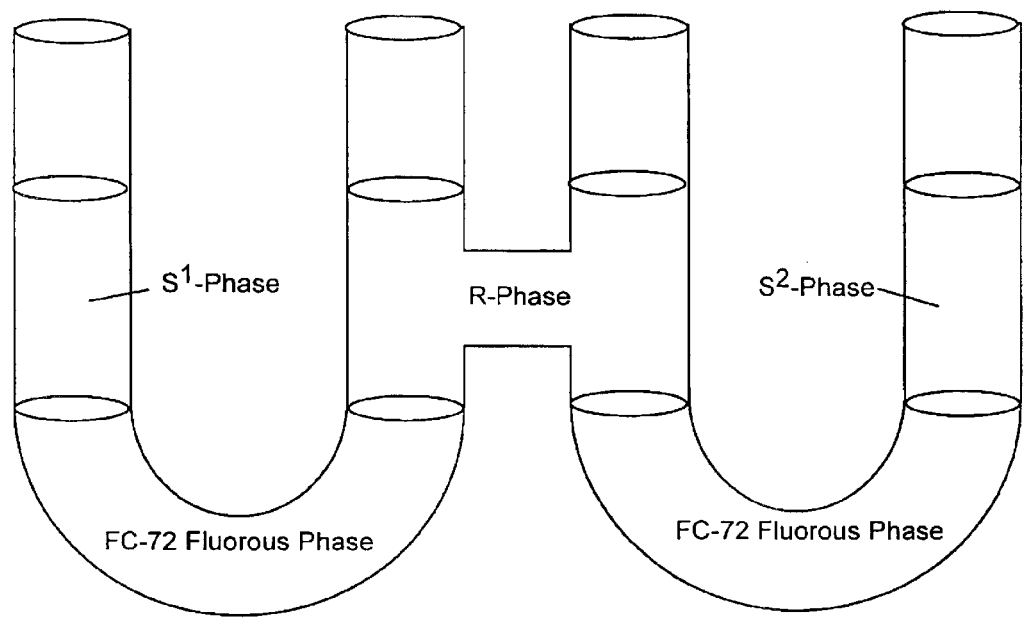
FIG. 14 illustrates an embodiment of a bromination reaction of two alkenes in sequential U-tubes.
Figure 14:
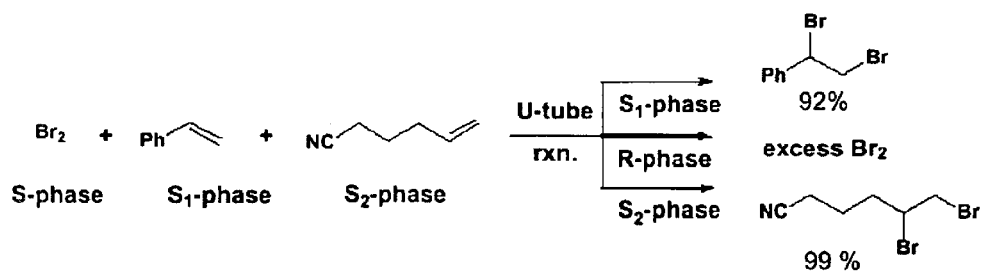

Parallel brominations are also possible as demonstrated by an experiment with sequential U-tubes. Separate benzene solutions of bromine, styrene and 5-hexenenitrile were placed in the R-, $S^1$- and $S^2$-phases, respectively, and those three phases were connected by FC-72 fluorous phases as illustrated in FIG. 14. The bromination reactions were complete after 2 days and (1,2-dibromoethyl)benzene and 5,6-dibromohexanenitrile were obtained from the $S^1$- and $S^2$-phases in 92% and 99% yields, respectively. In this example, the cross-contamination of products was not observed. This result indicates that the parallel bromination of several alkenes can be conducted by using multi-stage reactors with, for example, an octopus-shape. The ease and efficiency of adding bromine to only one place to conduct several reactions is evident.

Tables V and VI set forth examples of Friedel-Crafts additions to heteroaromatic and aromatic rings via fluorous triphasic reactions. The reaction methods resemble those shown in FIGS. 9 and 12. A benzene solution of the aromatic compound and the acid chloride or anhydride (upper phase) was added to FC-72 (middle phase) and neat tin tetrachloride (lower phase). The tin tetrachloride was gently stirred. Table V shows that acylations of thiophene with a number of acylating agents occur smoothly and in good yield. Likewise, an assortment of different aromatic rings have been acylated with propionyl chloride, and exemplary results are shown in Table VI. The slow delivery of the tin tetrachloride through the fluorous phase mitigates the rapid exotherms that occur on mixing in many Friedel-Crafts reactions. See, for example, Heaney, H. "The Bimolecular Aromatic Friedel-Crafts Reaction" In *Comprehensive Organic Synthesis;* B. M. Trost and I. Fleming, Ed.; Pergamon Press: Oxford, 1991; Vol. 2; pp 733. Heane, H. "The prehensive Organic Synthesis; B. M. Trost and I. Fleming, Ed.; Pergamon Press: Oxford, 1991; Vol. 2; pp 753. Eyley, S. C. "The Aliphatic Friedel-Crafts Reaction." In *Compre hensive Organic Synthesis;* B. M. Trost and I. Fleming, Ed.; Pergamon Press: Oxford, 1991; Vol. 2; pp 707.

Additional examples of cyclopropanation reactions are included in the Experimental Examples section, and triphasic or other multiphaxic variants of many other types of existing and new organic, organometallic and inorganic reactions are clearly advantageous.

TABLE V

Friedel-Crafts Acylation to Thiophene[a]

| entry | Acyl chloride | Product | Isolated[b] yield, % |
|---|---|---|---|
| 1 | | | 71 |
| 2 | | | 84 |
| 3 | | | 88 |
| 4 | | | 71 |
| 5 | | | 34 |
| 6 | | | 70 |
| 7 | Ac$_2$O | | 48 |

[a]Reaction conditions: 3 h, room temperature, slow stirring.
[b]The yields are based on thiophene.

TABLE VI
Friedel-Crafts Acylation to Aromatic Compounds[a]
| entry | Acyl chloride | Aromatic compound | Time, hr | Products | Isolated yield[b], % |
|---|---|---|---|---|---|
| 1 | 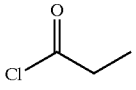 |  | 3 | 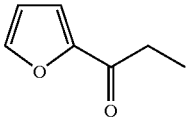 | 59[c] |
| 2 | | 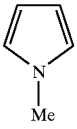 | 24 | 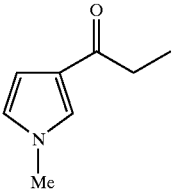 | 7[d] |
| | | | | 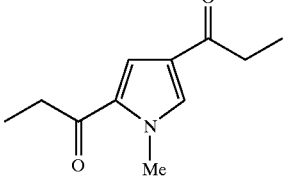 | 11[d] |
| 3 | | 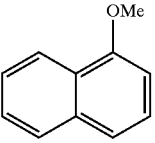 | 24 | 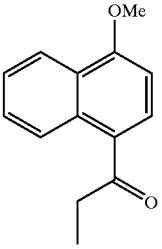 | 41 |
| 4 | | 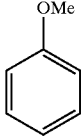 | 3 | 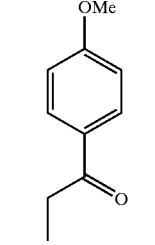 | 57[d] |
| | | | | 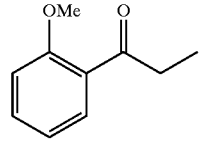 | 41[d] |
| 5 | | 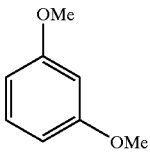 | 3 | 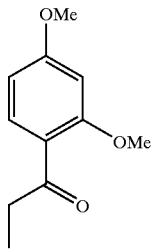 | 59 |

TABLE VI-continued

Friedel-Crafts Acylation to Aromatic Compounds[a]

| entry | Acyl chloride | Aromatic compound | Time, hr | Products | Isolated yield[b], % |
|---|---|---|---|---|---|

[a]Reaction conditions: room temperarture, slow stirring.
[b]The yields are based on aromatic conpounds.
[c]The yields are based on SnCl$_4$.
[d]The ratio of isomers are determined by $^1$H-NMR.

EXPERIMENTAL EXAMPLES

General Information $^1$H and $^{13}$C NMR spectra were recorded at 300 and 75 MHz, respectively, in CDCl$_3$. The chemical shifts are reported in δ units based on the solvent. IR spectra were obtained on a FT spectrophotometer. All commercially supplied chemicals were used without further purification. Column chromatography was performed with silica gel 60 (32–63 mesh). Dibromides obtained in the experiments were identified by comparison with authentic samples.

Example 1
Partition Coefficients of 1a

The partition coefficients of 1a were measured between FC-72 and various organic solvents. As used herein, the partition coefficient is defined generally as $[M]_{Fluorous}/[M]_{Non-Fluorous}$ or $[M]_F/[M]_{Non-F}$, wherein M is a molecule, compound or complex and $[M]_F$ is the concentration of the entity in the fluorous phase and $[M]_{Non-F}$ is the concentration of the entity in the non-fluorous phase (for example, organic phase) at equilibrium. In the experiments of Example 1 and Example 2, the partition coefficient is equal to the distribution coefficient.

To a solution of 1a (36.6 mg, 0.05 mmol) in an organic solvent (5 ml) was added FC-72 (5 ml) at 23° C. and the mixture was stirred for 3 h. Then, the concentrations in the fluorous and the organic solvents were determined by HPLC analysis. The partition coefficients were calculated as [FC-72]/[organic solvent]. The results are summarized in Table VII.

TABLE VII

Partition Coefficients of 1a at 23° C.
Between FC72 and an Organic Solvent

| organic solvent | partition coefficient |
|---|---|
| MeOH | 0.92 |
| EtOH | 0.91 |
| MeCN | 0.74 |
| DMF | 0.38 |
| CH$_2$Cl$_2$ | 0.14 |
| THF | 0.04 |

Example 2
Partition Coefficients of Various Fluorinated Silylethers

The partition coefficients of the fluorinated silylethers were measured between FC-72 and MeOH. In the case of the silylethers which have UV active (aromatic) functional groups, their partition coefficients were determined by the HPLC analysis method which is described as above. In the case of the silylethers which have no UV active functional groups, their partition coefficients were determined by measuring the weights of each phase after evaporation. The results are shown in Table I above Example 3
Transfer Rates of 2a between Two Organic Phases through an FC-72 Phase 2-(2-Naphtylethanol) 2a (10 mg) was dissolved in an organic solvent (1 ml) and the mixture was put into one side (side A) of U-tube 10 of FIG. 1, in which FC-72 (10 ml) was placed. The other organic solvent was put into the other side (side B) of U-tube 10 and the center phase (FC-72) was stirred (via, for example, magnetic stirring element 130) at 23° C. for 3 days without mixing the interfaces between the organic and FC-72 layers. The weights of each organic phase were measured after evaporation. The results are summarized in Table VIII.

TABLE VIII

Transfer Rates of 2a between Two Organic
Phases through an FC-72 Phase

| organic solvent (A)[a] | organic solvent (B) | ratio of 2a (A/B) |
|---|---|---|
| MeCN | MeCN | 99/1 |
| MeCN | THF | >99/1 |
| MeCN | MeOH | >99/1 |
| MeOH | MeCN | 99/1 |
| MeOH | THF | 96/4 |
| MeOH | MeOH | 99/1 |
| THF | THF | 90/10 |
| THF | MeOH | 97/3 |

[a]The organic solvent in side A in u-tube involved 2a at the beginning of the experiment.

Example 4
Transfer Rates of Organic Compounds Having Various Functional Groups in the Molecules between Two MeCN Phases through an FC-72 Phase Various organic compounds (0.1 mmol) were dissolved in MeCN (1 ml) and the mixture was put into one side (side A) of U-tube 10, in which FC-72 (10 ml) was placed. MeCN was put into the other side (side B) of U-tube 10 and the center phase (FC-72) was stirred at 23° C. for 3 days without mixing the interfaces between the organic and FC-72 layers. The weights of each organic phase were measured after evaporation. The results are summarized in Table IX.

TABLE IX

Transfer Rates of Various Organic Compounds between
Two MeCN Phases through an FC-72 Phase

| organic compound | ratio (A/B) |
|---|---|
| 2-naphthylethanol | 99/1 |
| 1-(2-naphthyl)ethanol | 96/4 |
| cinnamyl alcohol | 99/1 |
| dodecanol | 96/4 |
| 1-(1-naphthyl)ethylamine | 82/18 |
| 2-naphthyl acetate | 94/6 |
| 2-naphthylacetone | 91/9 |
| 2-naphthylacetonitrile | 99/1 |
| malononitrile | >99/1 |
| 2-naphthylacetic acid | >99/1 |
| 2-ethylnaphthalene | 66/33[a] |

[a]A slight amount of 2-ethylnaphthalene (~1%) was observed in FC-72.

Example 5a
Synthesis of Fluorinated Silylethers

A representative procedure for the synthesis of diisopropyl-1H,1H,2H,2H-perfluorodecanylsilyl 2-naphthylethyl ether 1a is described below. To a solution of 1H,1H,2H,2H-perfluoro-1-iododecane (8.0 g, 14 mmol) in dry ether (150 ml) at −78° C. under Ar was added t-BuLi (1.7 M in hexane; 35 ml, 21 mmol) dropwise with stirring. The mixture was stirred for 1.5 h at −78° C. and cholodiisopropylrosilane (1.7 ml, 10 mmol) was added to the reaction mixture dropwise. The mixture was stirred for 3 h and then warmed to ambient temperature. The reaction mixture was quenched with saturated $NH_4Cl$ aqueous solution and extracted with ether. The extract was dried over anhydrous $MgSO_4$ and concentrated. The dark red liquid residue was passed through short column chromatography on silica gel with hexane to provide diisopropyl-1H,1H,2H,2H-perfluorodecanylsilane in 95% yield (5.3 g, 9.5 mmol) as a colorless liquid. To a solution of diisopropyl-1H,1H,2H,2H-perfluorodecanylsilane (2.94 g, 4.0 mmol) in dry ether (50 ml) at 0° C. under Ar was added $Br_2$ (0.24 ml, 4.8 mmol) dropwise with stirring. The mixture was stirred for 30 min at 0° C. and evaporated. The residue was dissolved in $CH_2Cl_2$ (16 ml) and the solution was added to the mixture of 2-(2-naphthylethanol) (0.46 g, 2.7 mmol), 4-dimethylaminopyridine (12 mg, 0.10 mmol), and triethylamine (1.1 ml, 8.0 mmol) in $CH_2Cl_2$ (30 ml) dropwise at 0° C. with stirring. The mixture was stirred for 1.5 h and then water (50 ml) was added. The mixture was extracted with ether, dried over anhydrous $MgSO_4$ and concentrated. Purification by column chromatography on silica gel with hexane as eluent provided diisopropyl-1H,1H,2H,2H-perfluorodecanylsilyl 2-naphthylethyl ether (1a) in quantitative yield (2.0 g, 2.7 mmol) as a colorless liquid; $^1$H NMR ($CDCl_3$) δ 7.80 (t, J=6.7 Hz, 1H), 7.79 (d, J=8.5 Hz, 2H), 7.67 (s, 1H), 7.45 (m, 2H), 7.37 (dd, J=8.5, 1.2 Hz, 1 H), 3.97 (t, J=7.0 Hz, 2H), 3.03 (t, J=7.0 Hz, 2H), 2.05 (m, 2H), 1.03 (s, 14H), 0.82 (m, 2H); $^{13}$C NMR ($CDCl_3$) δ 136.5, 133.6, 132.3, 127.9, 127.7, 127.7, 127.5, 127.5, 126.0, 125.3, 122.2–107.2 (m), 64.7, 39.7, 25.4 (t, $^2J_{CF}$=23.6 Hz), 17.5, 17.4, 12.4, −0.35; IR(neat) 3058, 3020, 2946, 2869, 2733, 1206, 1151 cm$^{-1}$; HRMS (EI) m/z calcd for $C_{28}H_{29}OF_{17}Si$ 732.1716, found 732.1748.

Example 5b
Diisopropyl-1H,1H,2H,2-perfluorododecanylsilyl 2-naphthylethyl ether (1b)

Colorless liquid; $^1$H NMR ($CDCl_3$) δ 7.82 (t J=8.2 Hz, 1H), 7.79 (d, J=8.6 Hz, 2H), 7.67 (s, 1H), 7.46 (m, 2H), 7.46 (dd, J=8.6, 1.2 Hz, 1H), 3.98 (t, J=6.9 Hz, 2H), 3.03 (t, J=6.9 Hz, 2H), 2.05 (m, 2H), 1.03 (s, 14H), 0.83 (m, 2H); $^{13}$C NMR ($CDCl_3$) δ 136.6, 133.7, 132.4, 128.0, 127.8, 127.8, 127.6 (2), 126.1, 125.4, 119–107 (m), 64.8, 39.9, 25.5 (t, $^2J_{CF}$=23.4 Hz), 17.6, 17.5, 12.5, −0.23; IR(neat) 3057, 3022, 2946, 2869, 1222, 1153 cm$^-$; HRMS (EI) m/z calcd for $C_{30}H_{29}OF_{21}Si$ 832.1652, found 832.1624.

Example 5c
Diisopropyl-1H,1H,2H,2H-perfluorooctanylsilyl 2-naphthylethyl ether (1c)

Colorless liquid; $^1$H NMR ($CDCl_3$) δ 7.80 (t, J=7.1 Hz, 1H), 7.78 (d, J=8.7 Hz, 2H), 7.66 (s, 1H), 7.45 (m, 2H), 7.35 (dd, J=8.7, 1.3 Hz, 1H), 3.96 (t, J=6.9 Hz, 2H), 3.02 (t, J=6.9 Hz, 2H), 2.03 (m, 2H), 1.02 (s, 14H), 0.81 (m, 2H); $^{13}$C NMR ($CDCl_3$) δ 136.5 (d), 133.7 (d), 132.4 (d), 127.9, 127.7, 127.7, 127.5, 127.5, 125.9,125.3, 123.1–104.8 (m), 64.7, 39.7, 25.4 (t, $^2J_{CF}$=23.5 Hz), 17.4, 17.3, 12.4, −0.34; IR(neat) 3057, 2943, 2869, 2733, 1237, 1144 cm$^{-1}$; HRMS (EI) m/z calcd for $C_{26}H_{29}OF_{13}Si$ 632.1780, found 632.1791.

Example 6
Deprotection of the Fluorinated Silylethers 1 Using Triphasic Reaction System In a typical procedure for the fluorinated silylether 1a using modified U-tube 110 of FIGS. 2 and 3, a solution of diisopropyl-1H,1H,2H,2H-perfluorodecanylsilyl 2-naphthylethyl ether 1a (35 mg, 0.048 mmol) in MeCN (2 ml) was put into one side (S-phase) of U-tube 110, in which FC-72 (10 ml; F-phase) was placed and a solution of $H_2SiF_6$ (25% w in $H_2O$; 60 mg, 0.10 mmol) in MeOH was put into the other side (P-phase) of U-tube 110. Each phase (S-, F-, and P-phases) was stirred at room temperature and the reaction was monitored by TLC. After 20 h, the P-phase was decanted and poured into water. The mixture was extracted with ether, washed with saturated NaCl aqueous solution, and concentrated to give pure 2-(2-naphthylethanol) 2a in 92% yield (7.6 mg, 0.044 mmol).

Example 7
Purificative Deprotection of the Fluorinated Silylethers 1a in the Presence of 1-(2-naphthyl)ethanol Using Triphasic Reaction System A mixture of diisopropyl-1H,1H,2H,2H-perfluorodecanylsilyl 2-naphthylethyl ether 1a (72 mg, 0.10 mmol) and 1-(2-naphthyl)ethanol (3.4–17.2 mg, 0.02–0.10 mmol) in MeCN (2 ml) was put into one side (S-phase) of U-tube 110, in which FC-72 (10 ml; F-phase) was placed and a solution of $H_2SiF_6$ (25% w in $H_2O$; 60 mg, 0.10 mmol) in MeOH was put into the other side (P-phase) of U-tube 110. Each phase (S-, F-, and P-phases) was stirred at room temperature and the reaction was monitored by TLC. After 1a was consumed, the P-phase was decanted and poured into water. The mixture was extracted with ether, washed with saturated NaCl aqueous solution, and concentrated to give pure 2-naphthylethanol 2a in 86–92% yields. The S-phase was also decanted and concentrated. 1-(2-naphthyl)ethanol was recovered along with a small amount of 2a (>1–6% yields), as determined by $^1$H NMR.

Example 8
Purificative Deprotection of the Chiral Fluorinated Silylethers 1f and 1m in the Presence of the Corresponding Enantiomeric Alcohols Using a Triphasic Reaction System In a typical procedure for the purificative deprotection of the chiral fluorinated silylether if using modified U-tube 110, a mixture of diisopropyl-1H,1H,2H,2H-perfluorodecanylsilyl (S)-(−)-1-(2-naphthyl)ethyl ether 1f (72 mg, 0.10 mmol) and (R)-(+)-1-(2-naphthyl)ethanol (17 mg, 0.10 mmol) in MeCN (2 ml) was put into one side (S-phase) of U-tube 110, in which FC-72 (10 ml; F-Phase) was placed and a solution of $H_2SiF_6$ (25% w in $H_2O$; 60 mg, 0.10 mmol) in MeOH was put into the other side (P-phase) of U-tube 110. Each phase (S-, F-, and P-phases) was stirred at room temperature and the reaction was monitored by TLC. After 2, the P-phase was decanted and poured into water. The mixture was extracted with ether, washed with saturated NaCl aqueous solution, and concentrated to give 2f in 68% yield (12 mg, 0.068 mmol). The ee was determined by optical rotation analysis ($[\alpha]_D^{20}$−39° (c=0.34, MeOH), >97% ee). The S-phase was also decanted and concentrated to give 1-(2-naphthyl)ethanol in 99% yield (17 mg, 0.99 mmol, ($[\alpha]_D^{20}$+35° (c=0.65, MeOH), 90% ee). The total yield of 1-(2-naphthyl)ethanol was 85% based on the amount of both enantiomers in the reaction.

Example 8.1
Fluorous Palladium-catalyzed Coupling Reaction of (E)-Bromostyrene with Phenylzinc Iodide Using a Triphasic System A solution of the phosphine p-$C_6F_{13}CH_2CH_2C_6H_4)_3$P (100 mg, 0.08 mmol) in FC-72 (10 mL) was charged to the U-tube and Pd$_2$(dba)$_3$ (9 mg, 0.01 mmol) in benzene (1 mL) was added to the mixture. This biphasic mixture was stirred at room temperature until the palladium was extracted from the benzene solution into the FC-72 layer, and then the benzene layer was removed. A solution of (E)-bromostyrene in CH$_3$CN (1 mL) was charged to the S-phase of the U-tube and a solution of phenylzinc iodide (0.5 M in THF, 0.8 mL) was charged to the P-phase of the U-tube. After each phase was stirred for 1 day, H$_2$O was added to the S- and P-phases. Each reaction mixture of the S- and P-phases was extracted with ether, dried over MgSO$_4$ and evaporated. trans-Stilbene was obtained in 15% yield from the P-phase and (E)-bromostyrene was recovered from the S-phase.

Example 8.2
Control Experiment with a Non-fluorous Catalyst

FC-72 (10 mL) was charged to the U-tube (F-phase), a solution of (E)-bromostyrene (130 μL, 1.0 mmol) in MeCN (1 mL) was charged to the S-phase of the U-tube and a solution of Pd(PPh$_3$)$_4$ (23 mg, 0.02 mmol) in toluene (1.5 mL) was charged to the P-phase of the U-tube. After PhZnI (0.5 M in THF, 1.0 mL) was added to the P-phase, each phase was stirred for 1 day. The mixture in the P-phase was decanted into water, extracted with ether, dried over MgSO$_4$ and then evaporated. However, trans-stilbene was not obtained in the P-phase and (E)-bromostyrene was recovered from the S-phase.

Example 9
Selective Transport of a Fluorous-tagged Component of a Mixture

FC-72 (10 mL) was added to a U-tube. A mixture of 2-(2-naphthyl)ethanol 2a (17 mg, 0.1 mmol) and (3,3,4,4,5,5,5,6,6,7,7,8,8,9,9,10,10,10,10-heptadecafluorodecyl)-diisopropyl(3-phenyl-allyloxy)silane 1g (69 mg, 0.1 mmol) in acetonitrile (2 mL) was added on the top of FC-72 on one side of the U-tube (S-Phase). Acetonitrile (2 mL) was added on the top of FC-72 in the other side of the U-tube (P-Phase). All the three phases were kept stirred as illustrated in FIG. 4. The P-Phase was removed by syringe at various intervals and fresh acetonitrile (2 mL) was then added to the P-Phase side. The P-Phase collected from the U-tube was analyzed by TLC, weighing, and $^1$H NMR spectroscopy of the residue. TLC and $^1$H NMR showed the presence of the pure fluorous silyl ether 1g. 2-(2-naphthyl)ethanol was not detected by TLC or $^1$H NMR even after 1d. The weight of the residue obtained and the time after which the P-phase removed are given in the following table.

TABLE X

| Time (h) | Mass of the residue (mg) |
| --- | --- |
| 3 | 4.5 |
| 7 | 6 |
| 24 | 7 |

Example 10
Synthesis of 3b

The amine-containing receptor (0.3 mmol) 3a (FIG. 4) was dissolved in 100 ml of dry THF. Triethylamine 0.35 mmol (49 μl) was added. The solution was transferred to a 50 ml adding funnel. The solution is referred to as solution "1". In an another adding funnel, Krytox (DuPont) acid chloride 0.42 g (~0.17 mmol for MW 2500) was dissolved in 100 ml of 1,1,2-trichlorotrifluoroethane. The resulting solution is referred to as solution "2". In a 3-neck 500 ml round bottom flask, 50 ml of 1:1 v/v THF/1,1,2-trichlorotrifluoroethane was added and flushed with N$_2$. This is referred to as "3". Under nitrogen, and at room temperature, solution "2" and added to solution "1" were added simultaneously and dropwise to the well-stirred "3". After finishing the addition, the resultant mixture was stirred for an additional 18 hours.

After evaporating the solvent to dryness, 50 ml of 1,1,2-trichlorotrifluoroethane was added to the residue. The reaction mixture was shaken and sonicated well to extract 3b. The suspension was filtered, and the organic phase was washed with 0.5% NaHCO$_3$/H$_2$O. The resulting gel was dried in a vacuum oven at 50° C. The solid organic material was extracted with 1,1,2-trichlorotrifluoroethane, and the solvent evaporated to yield a yellow-colored viscous fluid.

In the U-tube transport experiments, the S- and P-phases were both 5 mL, while the F-phase was 10 mL. The F-phase was stirred continuously with a magnetic stirrer. The solute concentrations in the S-phase were in the millimolar range.

Example 11
Representative Bromination of Alkenes by the "Phase Vanishing" Method Bromine (0.68 g, 4.3 mmol) was added slowly to perfluorohexane (FC-72, 1.5 mL) in a test tube (13 mm 105 mm) and then cyclohexene (0.38 g, 4.6 mmol) in hexane (1.5 mL) was slowly poured into the test tube. The test tube was covered with aluminum foil to shield the reaction from light and kept at room temperature for 3 days. The hexane layer was decanted, washed with aqueous Na$_2$S$_2$O$_3$, dried over MgSO$_4$, and concentrated. The residue was purified by short SiO$_2$ column chromatography (10 mm×40 mm) with hexane to give trans-1,2-dibromocyclohexane in 88% yield. Data for a series of similar experiments are shown in Table III.

Example 12
Representative U-tube Bromination of Alkenes

A solution of styrene (52 mg, 0.5 mmol) in benzene (2 mL) was put into one side (S-phase) of the U-tube containing FC-72 (10 mL; F-phase), and a solution of Br$_2$ (50 μl, 1.0 mmol) in benzene (1 mL) was placed into the other side (R-phase) of the U-tube. The U-tube reactor was covered with aluminum foil to shield from light. The F-phase was stirred at room temperature until the color of the S-phase became red. After 19 h, the S-phase was decanted and poured into aqueous Na$_2$S$_2$O$_3$ solution. The mixture was extracted with ether, washed with saturated NaCl aqueous solution, and concentrated. Pure 1,2-dibromoethylbenzene was obtained in 95% yield (125 mg, 0.48 mmol). The results of a series of similar experiments are shown in Table IV.

Example 13
Representative Parallel Bromination Reaction by Using a Sequential U-tube Reactor FC-72 (10 mL; F-phase) was placed in both necks of a sequential U-tube reactor (FIG. 6). A solution of styrene (60 μl, 0.52 mmol) in benzene (2 mL) was placed in the left side of the sequential U-tube reactor (S$^1$-phase), and a solution of 5-hexenenitrile (60 μl, 0.53 mmol) in benzene (2 mL) was placed in its right side (S$^2$-phase). Br$_2$ (150 μl, 3.0 mmol) in benzene (4 mL) was poured into the center (R-phase) of the reactor. The reactor was covered with aluminum foil to shield from light. The fluorous phases were gently stirred at room temperature until the color of the S-phases became red. After 2 days, the S-phases were decanted and poured into aqueous Na$_2$S$_2$O$_3$ solution. Each mixture was extracted with ether, washed with saturated NaCl aqueous solution, and concentrated. Pure 1,2-dibromoethylbenzene and 5,6-dibromehexanenitrile were obtained in 92% yield (127 mg, 0.48 mmol) from $S^1$-phase and in 99% yield (126 mg, 0.52 mmol) from $S^2$-phase, respectively.

Example 14
Representative Friedel-Crafts Acylation by the Phase-Vanishing Method The procedure for the Friedel-Crafts acylation of thiophene with propionyl chloride in the presence of tin tetrachloride is as follows. Tin tetrachloride (630 mg, 2.4 mmol) was added slowly to perfluorohexanes (FC-72, 3 mL) in a test tube (14 mm×105 mm) and then a mixed benzene solution (3 mL) of thiophene (168 mg, 2.0 mmol) and propionyl chloride (185 mg, 2.0 mmol) was slowly poured into the test tube. The tin tetrachloride layer in the bottom was stirred gently so as not to mix the three phases. which disappeared after 3 h. The benzene layer was decanted, washed with 10% HCl and $H_2O$, dried over $MgSO_4$, and concentrated. The residue was purified by short column chromatography (10 mm×40 mm) on silica gel with benzene to give 2-propionylthiophene in 71 % yield (200 mg).

Example 15
Representative Phase-Vanishing Cyclopropanation of Alkenes with Diethyzinc and Methylene Diiodide Diiodomethane(120 µl, 1.5 mmol) was added slowly to perfluorohexanes (FC-72, 3 mL) in a test tube (14 mm×105 mm) and then trimethylsiloxycyclohexene (180 mg, 1.05 mmol) in hexane (3.5 mL) was slowly poured into the test tube. A hexane solution of diethylzinc (1.0 M, 1.5 mmol, 1.5 mmol) was added to the hexane layer, and the diiodomethane layer on the bottom was stirred gently so as not to mix the three phases. After 10 h at room temperature, additional diiodomethane (40 µl, 0.5 mmol) was added to the bottom layer of the test tube by using a syringe. After 14 h, the reaction mixture was cooled to 0° C., and saturated $NH_4Cl$ (10 mL) was added. The hexane layer was decanted, washed with $H_2O$, dried over $MgSO_4$, and concentrated in vacuo. The residue was purified by short column chromatography (17 mm×20 mm of florisil layer over 50 mm of silica gel layer) with benzene/hexane: ¼ to give 1-trimethylsiloxybicyclo[4.1.0]heptane in 63% yield (123 mg).

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of reacting a first non-fluorous compound to produce a second non-fluorous compound comprising the steps of:
contacting a first non-fluorous phase including the first non-fluorous compound with a first fluorous phase at a first phase interface, the first non-fluorous compound distributing between the first fluorous phase and the first non-fluorous phase;
contacting the first fluorous phase with a second non-fluorous phase at a second phase interface; and
including at least a third non-fluorous compound in the second non-fluorous phase that reacts with the first non-fluorous compound to produce the second non-fluorous compound, the second non-fluorous compound having a distribution coefficient less than the first non-fluorous compound.

2. The method of claim 1 one wherein at least one of the first non-fluorous phase and the second non-fluorous phase is an aqueous phase.

3. The method of claim 1 wherein at least one of the first non-fluorous phase and the second non-fluorous phase is an organic phase.

4. The method of claim 1 wherein the first non-fluorous phase is a first organic phase and the second non-fluorous phase is a second organic phase.

5. The method of claim 1 wherein the first non-fluorous phase also includes at least one non-fluorous compound other than the first non-fluorous compound, the other compound having a distribution coefficient less than the first non-fluorous compound.

6. The method of claim 5 wherein the other non-fluorous compound has a distribution coefficient substantially less than the first non-fluorous compound.

7. The method of claim 6 wherein the first non-fluorous compound has a distribution coefficient in the first organic phase between approximately 0.01 and approximately 10.

8. The method of claim 1 further comprising the step of contacting the second non-fluorous phase with a second fluorous phase at a third phase interface.

9. The method of claim 8 further comprising the step of contacting the second fluorous phase with a third non-fluorous phase at a fourth phase interface.

10. The method of claim 1 further comprising the step of perturbing at least one of the first phase interface and the second phase interface.

11. The method of claim 4 further comprising the step of perturbing at least one of the first phase interface and the second phase interface.

12. The method of claim 1 wherein the first non-fluorous compound is dibromine.

13. The method of claim 12 wherein the second non-fluorous compound is an alkene or an alkyne.

14. A method of reacting a first non-fluorous compound with at least a second non-fluorous compound to produce a third non-fluorous compound comprising the steps of:
contacting a first non-fluorous phase including the first non-fluorous compound and the second non-fluorous compound with a first fluorous phase at a first phase interface;
contacting the first fluorous phase with a second non-fluorous phase at a second phase interface; and
including at least one non-fluorous reagent to promote the reaction between the first non-fluorous compound and the second non-fluorous compound in the second non-fluorous phase, the non-fluorous catalyst distributing between the first fluorous phase and the second non-fluorous phase.

15. The method of claim 14 wherein at least one of the first non-fluorous compound and the second non-fluorous compound has a distribution coefficient less than the non-fluorous reagent.

16. The method of claim 15 wherein the non-fluorous reagent is a metal halide catalyst.

17. The method of claim 16 wherein the reaction between the first fluorous compound and the second fluorous compound is a Friedel-Crafts reaction.

18. The method of claim 16 wherein the catalyst is tin tetrachloride.

19. A method of separating a mixture of at least a first non-fluorous compound arid a second non-fluorous compound comprising the steps of:
contacting a mixture of the of the first non-fluorous compound and the second non-fluorous compound in a first non-fluorous phase with a first fluorous phase at a first phase interface, the first non-fluorous compound distributing between the first fluorous phase and the first non-fluorous phase, the second non-fluorous compound having a distribution coefficient less than the first non-fluorous compound; and contacting the fluorous phase with a second non-fluorous phase at a second phase interface.

20. The method of claim 19 one wherein at least one of the first non-fluorous phase and the second non-fluorous phase is an aqueous phase.

21. The method of claim 19 wherein at least one of the first non-fluorous phase and the second non-fluorous phase is an organic phase.

22. The method of claim 19 wherein the first non-fluorous phase is a first organic phase and the second non-fluorous phase is a second organic phase.

23. The method of claim 19 further comprising the step of contacting the second non-fluorous phase with a second fluorous phase at a third phase interface.

24. The method of claim 23 further comprising the step of contacting the second fluorous phase with a third non-fluorous phase at a fourth phase interface.

25. The method of claim 23 further comprising the step of drawing off a portion of second non-fluorous phase containing the first non-fluorous compound and adding non-fluorous solvent that does not contain the first non-fluorous compound.

* * * * *